(12) United States Patent
Morgan et al.

(10) Patent No.: US 7,369,901 B1
(45) Date of Patent: May 6, 2008

(54) MYOCARDIAL LEAD AND LEAD SYSTEM

(75) Inventors: Kevin L. Morgan, Simi Valley, CA (US); John R. Helland, Saugus, CA (US); Sheldon Williams, Green Valley, CA (US); Yougandh Chitre, Valencia, CA (US); Andrew W. McGarvey, Los Angeles, CA (US); Christopher Fleck, Canyon Country, CA (US); Jnyan Patel, Burbank, CA (US); Scott Salys, Los Angeles, CA (US); Kerwyn Schimke, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 11/056,666

(22) Filed: Feb. 10, 2005

Related U.S. Application Data

(60) Provisional application No. 60/543,897, filed on Feb. 11, 2004.

(51) Int. Cl.
*A61N 1/362* (2006.01)
*A61N 1/05* (2006.01)

(52) U.S. Cl. .................. 607/127; 607/116; 607/119; 607/122; 607/131; 600/375; 600/377

(58) Field of Classification Search ............... 607/116, 607/119, 122–3, 126–7, 129–31; 600/373–75, 600/37
See application file for complete search history.

(56) References Cited

U.S. PATENT DOCUMENTS

| 4,187,853 A | 2/1980 | Barton et al. | |
|---|---|---|---|
| 4,270,549 A | 6/1981 | Heilman | 128/784 |
| 4,381,013 A * | 4/1983 | Dutcher | 607/127 |
| 4,402,330 A * | 9/1983 | Lindemans | 607/122 |
| 4,616,652 A | 10/1986 | Simpson | |
| 4,624,266 A | 11/1986 | Kane | 128/785 |
| 4,628,943 A | 12/1986 | Miller | |
| 4,637,377 A | 1/1987 | Loop | 128/1 R |
| 4,667,686 A * | 5/1987 | Peers-Travarton | 607/127 |
| 4,765,341 A | 8/1988 | Mower et al. | 128/785 |
| 4,892,102 A | 1/1990 | Astrinsky | 128/642 |
| 4,976,689 A | 12/1990 | Buchbinder et al. | |
| 5,143,090 A | 9/1992 | Dutcher et al. | |
| 5,217,028 A | 6/1993 | Dutcher et al. | |
| 5,246,014 A * | 9/1993 | Williams et al. | 607/122 |
| 5,336,252 A | 8/1994 | Cohen | 607/119 |
| 5,409,469 A | 4/1995 | Schaerf | 604/282 |

(Continued)

OTHER PUBLICATIONS

NonFinal Office Action, mailed Aug. 15, 2007: Related U.S. Appl. No. 11/056,751.

(Continued)

*Primary Examiner*—Carl Layno
*Assistant Examiner*—Natasha Patel

(57) ABSTRACT

An implantable myocardial stimulation lead comprises a lead body having a distal end and a proximal end, and an electrical connector carried by the proximal end of the lead body. An electrode header carried by the distal end of the lead body has an axis and includes a helical fixation element extending along the axis, the electrode header having a surface configured to receive a driver for rotating the electrode header to screw the helical fixation element into the tissue of the heart. The lead body carries along its length a strain relief member resisting excessive bending of the lead body.

16 Claims, 39 Drawing Sheets

U.S. PATENT DOCUMENTS

| | | | |
|---|---|---|---|
| 5,464,447 A | 11/1995 | Fogarty et al. | 607/129 |
| 5,472,438 A | 12/1995 | Schmit et al. | 606/1 |
| 5,476,502 A | 12/1995 | Rubin | 607/127 |
| 5,522,874 A | 6/1996 | Gates | 607/127 |
| 5,522,875 A | 6/1996 | Gates et al. | 607/127 |
| 5,522,876 A | 6/1996 | Rusink | 607/127 |
| 5,588,951 A | 12/1996 | Zhu et al. | 600/207 |
| 5,618,287 A | 4/1997 | Fogarty et al. | 606/129 |
| 5,658,327 A * | 8/1997 | Altman et al. | 607/127 |
| 5,735,791 A | 4/1998 | Alexander, Jr. et al. | 600/37 |
| 5,776,178 A | 7/1998 | Pohndorf et al. | 607/127 |
| 5,800,394 A | 9/1998 | Yoon et al. | 604/101 |
| 5,837,007 A | 11/1998 | Altman et al. | 604/127 |
| 5,871,532 A | 2/1999 | Schroeppel | 607/128 |
| 5,904,711 A | 5/1999 | Flom et al. | 607/129 |
| 6,010,526 A | 1/2000 | Sandstrom et al. | |
| 6,015,382 A | 1/2000 | Zwart et al. | 600/207 |
| 6,036,640 A | 3/2000 | Corace et al. | 600/207 |
| 6,146,401 A | 11/2000 | Yoon et al. | 606/192 |
| 6,259,953 B1 | 7/2001 | Lucchesi et al. | 607/119 |
| 6,259,954 B1 | 7/2001 | Conger et al. | 607/122 |
| 6,321,102 B1 | 11/2001 | Spehr et al. | 600/374 |
| 6,324,415 B1 | 11/2001 | Spehr et al. | 600/374 |
| 6,355,027 B1 | 3/2002 | Le et al. | 604/525 |
| 6,408,214 B1 | 6/2002 | Williams et al. | 607/122 |
| 6,776,765 B2 | 8/2004 | Soukup et al. | |
| 6,819,959 B1 * | 11/2004 | Doan et al. | 607/127 |
| 6,923,807 B2 * | 8/2005 | Ryan et al. | 606/41 |
| 2002/0032456 A1 | 3/2002 | Jervis | 606/190 |
| 2003/0074041 A1 | 4/2003 | Parry et al. | 607/130 |
| 2003/0212446 A1 | 11/2003 | Kaplan et al. | |
| 2005/0004644 A1 | 1/2005 | Kelsch et al. | |

OTHER PUBLICATIONS

NonFinal Office Action, mailed Mar. 20, 2007: Related U.S. Appl. No. 11/056,775.

Final Office Action, mailed Sep. 18, 2007: Related U.S. Appl. No. 11/056,775.

\* cited by examiner

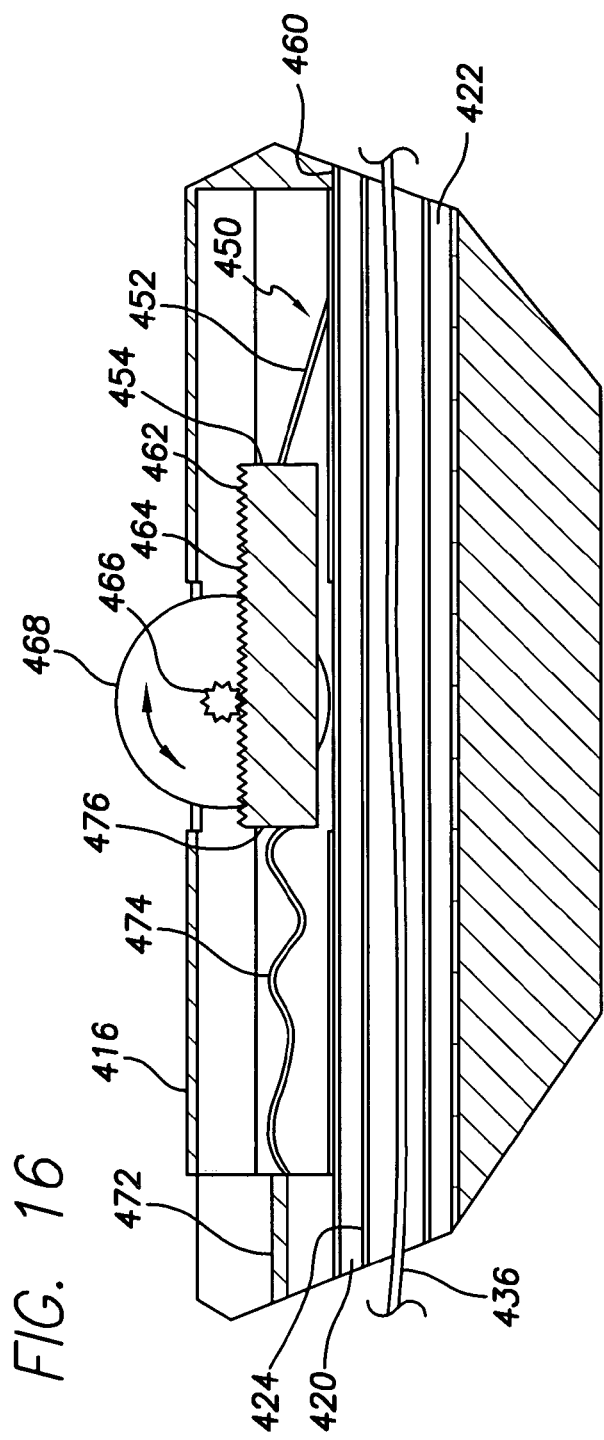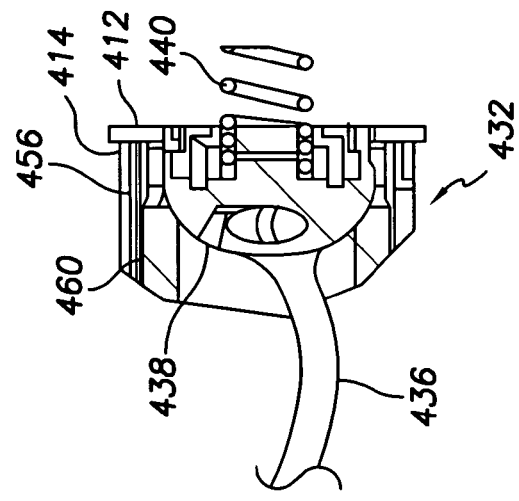

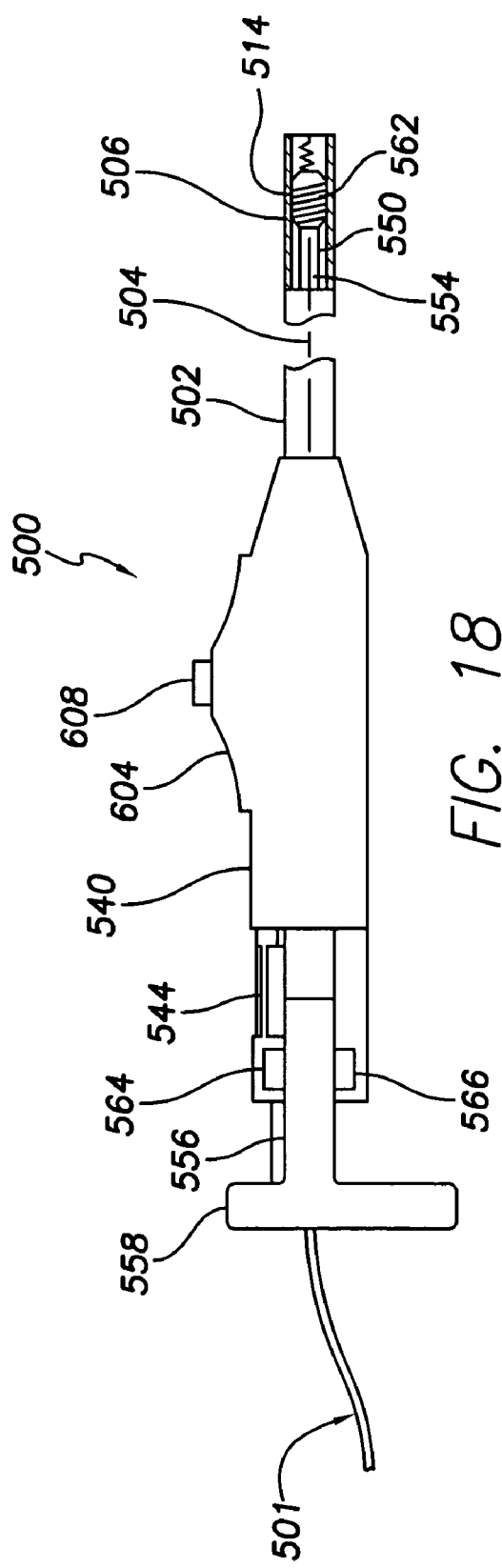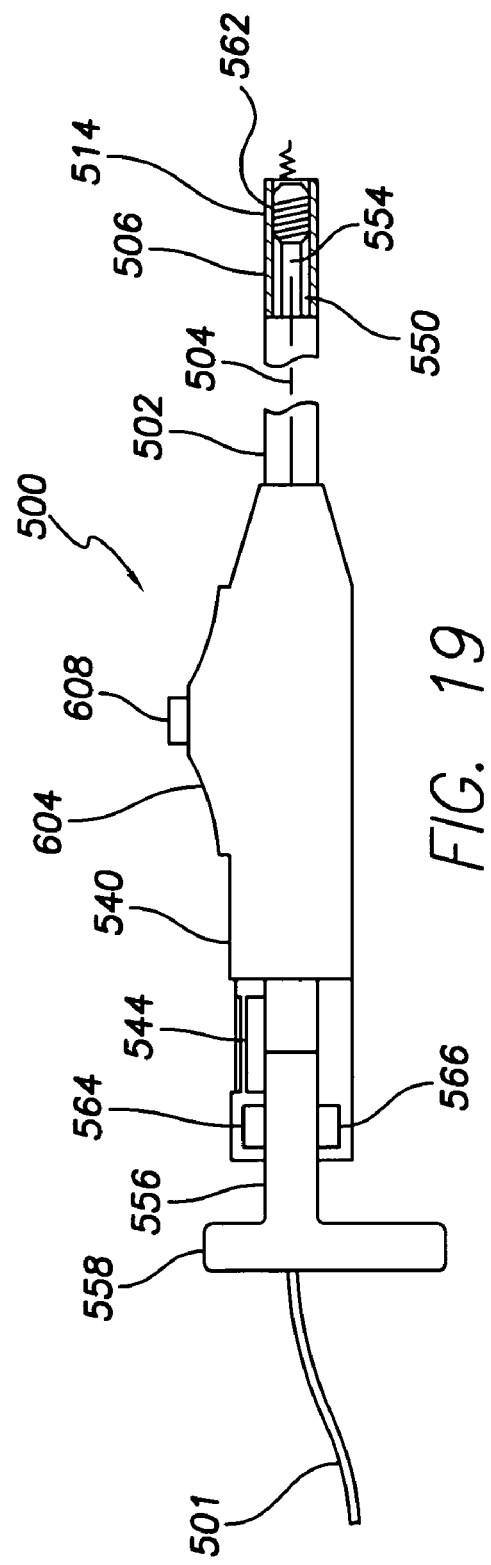

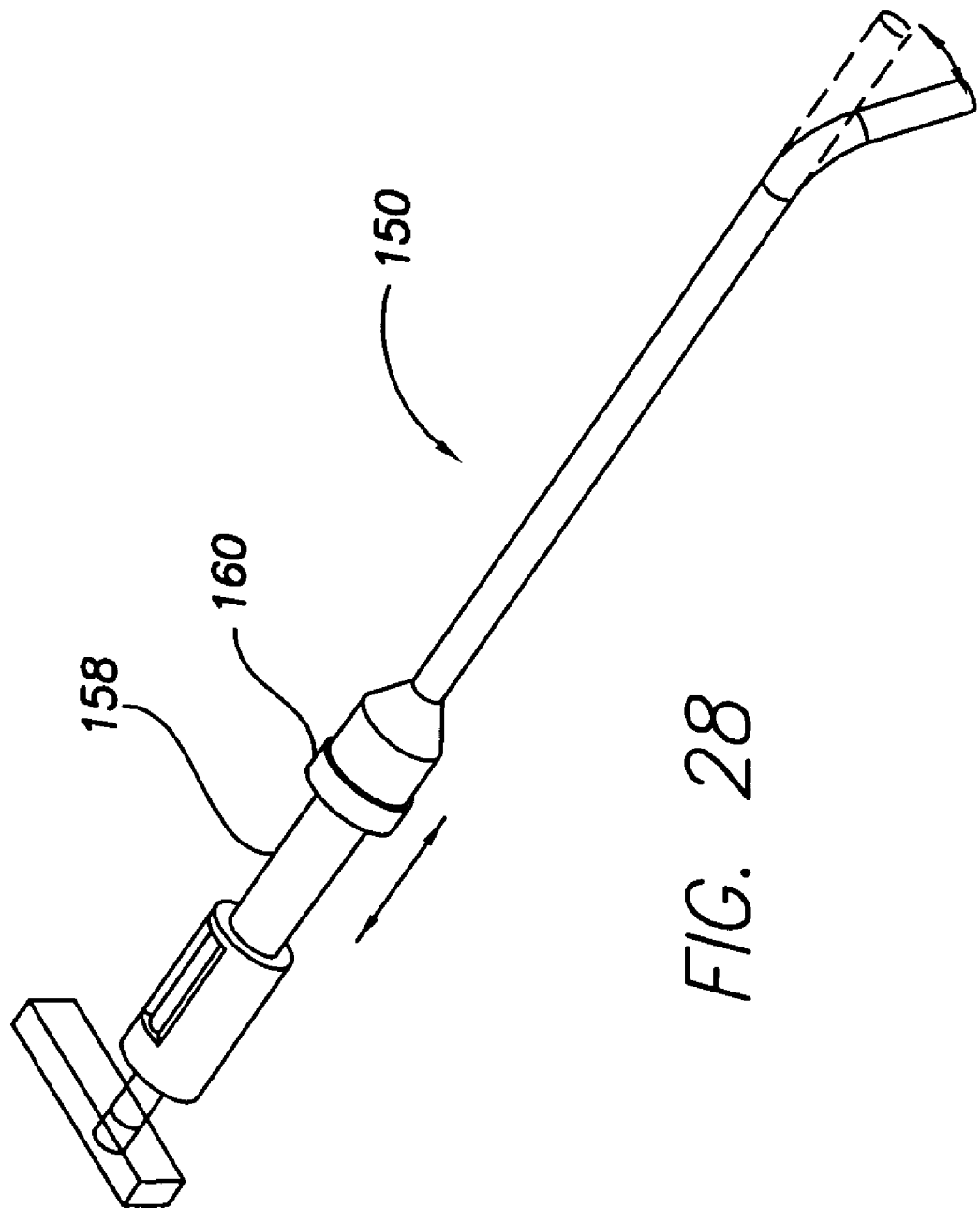

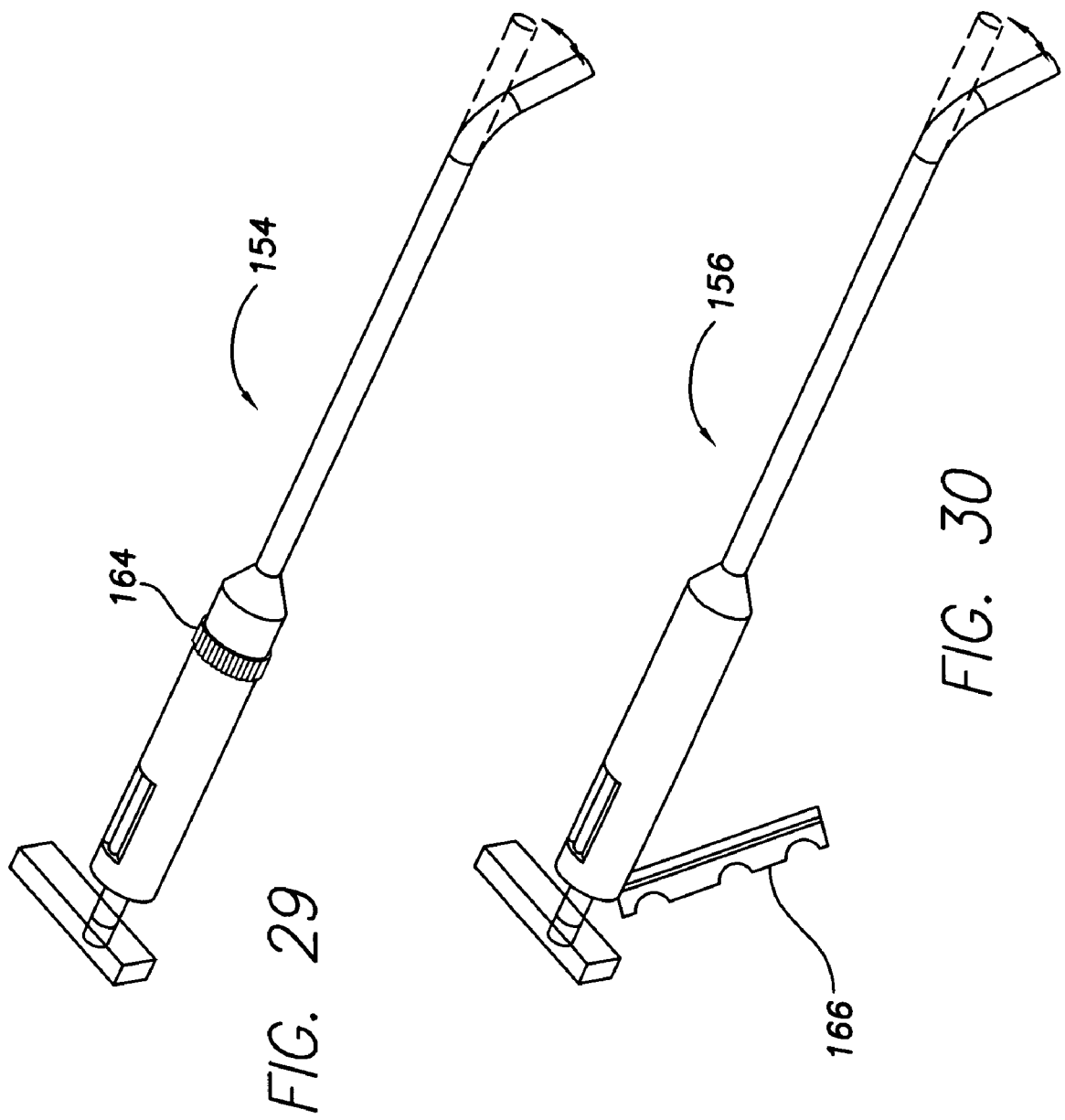

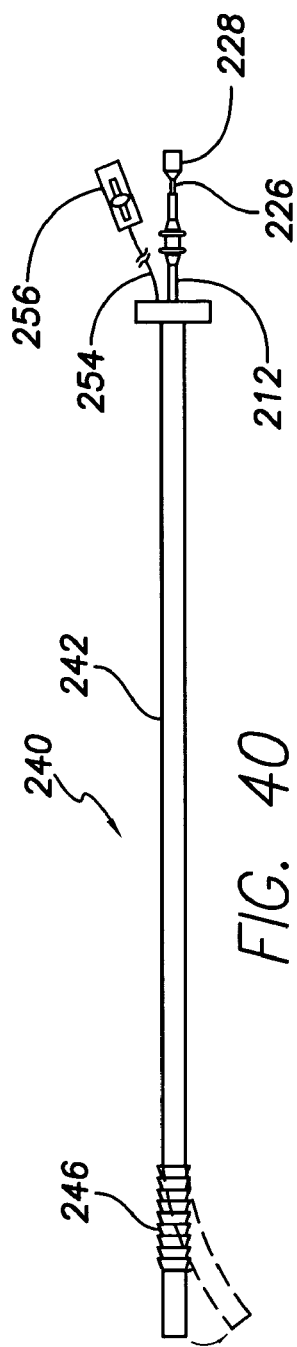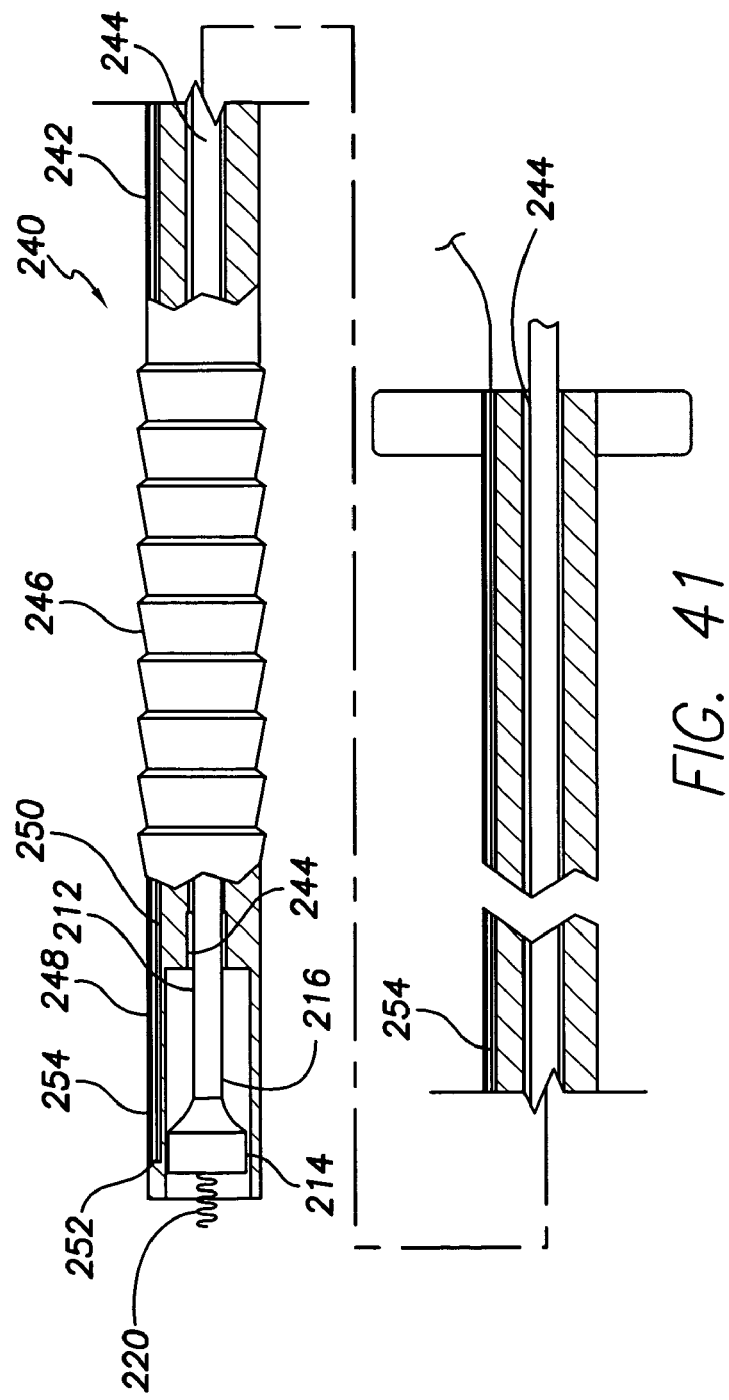
FIG. 40
FIG. 41

MYOCARDIAL LEAD AND LEAD SYSTEM

CROSS REFERENCE TO RELATED APPLICATIONS

This application claims the benefit of U.S. Provisional Application No. 60/543,897, filed Feb. 11, 2004, titled "Myocardial Lead System"; and is related to U.S. patent applications:

1) Ser. No. 11/056,751, titled "Myocardial Lead and Lead System"; and

2) Ser. No. 11/056,775, titled "Myocardial Lead and Lead System"; both of which also claim the benefit of U.S. Provisional Application No. 60/543,897, filed Feb. 11, 2004; all applications filed concurrently herewith.

FIELD OF THE INVENTION

The present invention relates generally to myocardial lead systems and particularly to improved myocardial leads and apparatus for delivering and implanting such leads.

BACKGROUND OF THE INVENTION

When an implantable cardiac stimulation and/or sensing lead is placed on the outer surface of the heart in a process known as epi-myocardial lead implantation, the heart is made accessible by entering through the chest wall. The two most commonly used procedures have been the left lateral thoracotomy (exposing the left ventricle (LV)) and the subxiphoid (or subcostal) approach (allowing direct access to the apical area of the right ventricle (RV)).

The left lateral thoracotomy (or "mini thoracotomy") technique requires an incision usually in the left fourth or fifth intercostal space. The cut-down is made sufficiently large to allow adequate access to the left side or left ventricle (LV) of the heart. The incision can be long or short (physician's preference) and is made from a point near the left parasternal border to a point near the left anterior axillary line (between the sternum and the armpit). The LV is fairly well accessible with this approach. Either screw-in sutureless myocardial leads or suture-on epicardial leads have generally been used in this approach.

The subxiphoid or subcostal approach allows access to the heart without a formal or full thoracotomy. In this approach the incision is made just below the rib cage (subcostal approach) or just below the xiphoid (subxiphoid approach). With this latter approach especially, screw-in sutureless myocardial leads can easily be placed near the apex of the RV and in some cases, on a small, limited portion of the LV.

These epi-myocardial lead implant approaches, although having potential for some significant morbidities, have been suitable over the years for the relatively few patients requiring such leads (usually pediatrics and the few adults having mechanical valves which contra-indicate use of conventional transvenous leads). However, with the rapid growth of cardiac resynchronization therapy (CRT) in congestive heart failure (CHF) patients, there is now a need to be able to reliably and quickly place a lead with a myocardial electrode on the LV. The reason for this is that in a certain percentage of CRT patients (ranging from about 5 to 15%) subjected to the current transvenous approach of implanting leads into the coronary veins (1) the coronary sinus os (the opening into the coronary sinus from the right atrium) cannot be cannulated to allow a lead to be inserted into the coronary sinus and coronary veins, or (2) the coronary venous anatomy is too tortuous for the lead to be able to be positioned into the appropriate LV coronary vein target site, or (3) the lead's electrode lands in a coronary venous site with poor, unacceptable parameters, for example, high pacing thresholds, phrenic nerve stimulation, and/or poor activation sequence/poor hemodynamics. Thus, there is a major need in the clinical realm to use myocardial leads via a transthoracic approach to place lead electrodes on the LV in such patients.

Conventional implant approaches using current epi-myocardial leads have disadvantages including the relatively large incisions needed to gain access into the thoracic cavity and to the heart's LV; the difficulty of quickly and easily attaching the lead; the higher rate of morbidity, trauma and pain to the patient; the occurrence of undetectable bleeding in the thoracic cavity due to the larger incisions; the tendency to require longer recovery time in the hospital; and cosmetic disagreeability to the patients.

Hand manipulated tools called lead introducers are used to implant screw-in or helix fixation electrodes in the cardiac tissue. Presently available lead introducers for implanting the helix electrodes of myocardial pacing leads tend to be large diameter, stiff structures designed to handle myocardial leads having lead bodies that extend radially outwardly from an electrode header. Examples of this kind of tool and lead body/header interconnection are disclosed in U.S. Pat. No. 4,972,847 issued Nov. 27, 1990, and titled "Pacing Lead and Introducer Therefor." While lead bodies that extend radially outward from the electrode header at the junction thereof tend to conform more closely to the outer surface of the heart after implantation, the lead body is often subjected to high stresses during implantation because of the sharp bend imposed upon the lead body when the electrode header is temporarily held inside the introducer. In addition, the distal portion of the lead body extending from the electrode header is usually captured in a longitudinal groove extending along the length of the introducer thereby causing the lead to wrap around the outside of the introducer as it is rotated to advance the helix electrode into the myocardium. Introducers of this kind also tend to be relatively complex, comprising multiple parts that must be unlocked to release the lead and its electrode header from the introducer following implantation.

Myocardial leads whose lead bodies extend axially from the electrode header are also available. Although these kinds of leads tend to be more easily implanted, the lead bodies are often subjected to tight bends following implantation in order for the lead body to lie against the outer surface of the heart and follow the contour thereof. Such orientations can result in high stresses and fatigue damage at or near the lead body/electrode header interface.

SUMMARY OF THE INVENTION

In accordance with one specific, exemplary embodiment of the invention, there is provided an implantable myocardial stimulation lead comprising a lead body having a distal end and a proximal end, and an electrical connector carried by the proximal end of the lead body. An electrode header carried by the distal end of the lead body has an axis and includes a helical fixation element extending along the axis, the electrode header having a surface configured to receive a driver for rotating the electrode header to screw the helical fixation element into the tissue of the heart. In accordance with one particular form of the invention, the lead body and the electrode header are joined at a junction, the lead body extending proximally from the junction in a direction intermediate the direction of the header axis and the direction of a second axis transverse to the header axis. This geometry minimizes stress at the junction during implantation of the lead.

Pursuant to another specific, exemplary embodiment of the present invention, there is provided an implantable myocardial stimulation lead comprising a lead body having a distal end and a proximal end. The proximal end carries an electrical connector and the distal end carries an electrode header. The electrode header has an axis and includes a helical fixation element extending along the axis. The electrode header further has a surface configured to receive a driver for rotating the electrode header to screw the helical fixation element into the tissue of the heart. The distal end of the lead body has a flexible section extending from said electrode header, the flexible section providing strain relief. Preferably, the flexible section comprises a plurality of longitudinally spaced apart projections, adjacent projections interfering with one another upon bending of the distal end of the lead body through a predetermined radius of curvature to provide the mentioned strain relief.

Pursuant to yet another embodiment of the present invention, there is provided an implantable myocardial stimulation lead comprising a lead body having a distal end and a proximal end, an electrical connector being carried by the proximal end of the lead body; and an electrode header being carried by the distal end of the lead body. The electrode header has an axis and includes a helical fixation element extending along the axis. The electrode header further has a surface configured to receive a driver for rotating the electrode header to screw the helical fixation element into the tissue of the heart. Last, the distal end of the lead body carries a strain relief member resisting excessive bending of the lead body. In accordance with one form thereof, the strain relief member may comprise a longitudinally disposed strain relief coil extending proximally of the distal end of the lead body; preferably, the strain relief coil extends the entire distance between the distal and proximal ends of the lead body.

In yet another exemplary embodiment of the present invention, an implantable myocardial stimulation lead is provided that comprises a lead body having a proximal end, a distal end, an electrical connector carried by the proximal end, and an electrode header carried by the distal end. The electrode header has an axis and includes a helical fixation element extending along the axis, the helical fixation element comprising a first portion within the confines of the electrode header and a second portion projecting from the electrode header. The second portion of the helical fixation element comprises a plurality of turns having a substantially constant outer diameter. Preferably, the first portion of the helical fixation element carries a drug-eluting device.

In accordance with yet another specific, exemplary embodiment of the invention, there is provided an implantable myocardial stimulation lead comprising a lead body having a distal end, a proximal end, an electrical connector carried by the proximal end of the lead body, and an electrode header carried by the distal end. The electrode header includes a helical fixation element having a portion projecting from a surface of the electrode header. The electrode header surface carries a tissue ingrowth-promoting mesh adapted to engage the myocardial tissue. Pursuant to one form of this embodiment, the mesh has an annular configuration extending about the helical fixation element. Preferably, the mesh is made of thin, texturized polyester yarn.

Pursuant to another specific, exemplary embodiment of the invention, there is provided an introducer for facilitating the thoracoscopic delivery and implantation of an electrode header on the distal end of the lead body of a myocardial stimulation lead, the electrode header including a helical fixation element. The introducer comprises an elongated, tubular introducer body having a deflectable or steerable distal end section. A lumen extending the length of the introducer body is adapted to receive within the steerable distal end section of the introducer body a driver configured to mate with and drivingly implant the electrode header. By placing the lead body inside the tubular structure of the introducer body, wrapping of the lead body about the exterior of the introducer during lead implantation is avoided.

In accordance with yet another specific, exemplary aspect of the invention, there is provided a system for the minimally invasive implantation of a myocardial lead having an electrode header carrying a helical fixation element at a distal end of the lead. The system comprises a plurality of instruments including a lead introducer having a distal end section adapted to steer and deliver the header to a selected implantation site on the myocardium; a thoracoscope for observing the instruments of the system during the minimally invasive implantation; and an inflatable heart jack for elevating the heart to provide access to remote regions of the heart's surface.

BRIEF DESCRIPTION OF THE DRAWINGS

The foregoing and other objects, features and advantages of the invention will be evident to those skilled in the art from the detailed description below, taken together with the accompanying drawings, in which:

FIG. 16 is an enlargement of a portion of the side view shown in FIG. 15;

FIG. 17 is an enlargement of another portion of the side view of FIG. 15;

FIG. 18 is a side view, partly in section, of a steerable introducer in accordance with another specific, exemplary embodiment of the invention, showing an electrode header driver and electrode header carried thereby in a fully retracted position;

FIG. 19 is a side view of the steerable introducer of FIG. 18 showing the electrode header driver and electrode header carried thereby in a fully advanced or extended position;

FIGS. 28-30 are perspective views of alternative embodiments of the introducer of the present invention;

FIG. 40 is a side view of an alternative embodiment of the introducer of the invention for inserting and implanting a myocardial lead of the kind illustrated in FIG. 35;

FIG. 41 is an enlarged side view, partly in cross section, of the introducer of FIG. 40;

DETAILED DESCRIPTION OF THE INVENTION

The following description is of a best mode presently contemplated for practicing the invention. This description is not to be taken in a limiting sense but is made merely for the purpose of describing the general principles of the invention whose scope is defined by the appended claims. Although the invention will be described in the context of implantable cardiac stimulation and sensing leads, it will be evident to those skilled in the art that the invention described herein has broader utility, being applicable to a wide variety of implantable medical leads for stimulating selected body tissue and sensing the electrical activity of such tissue.

Figure 1:
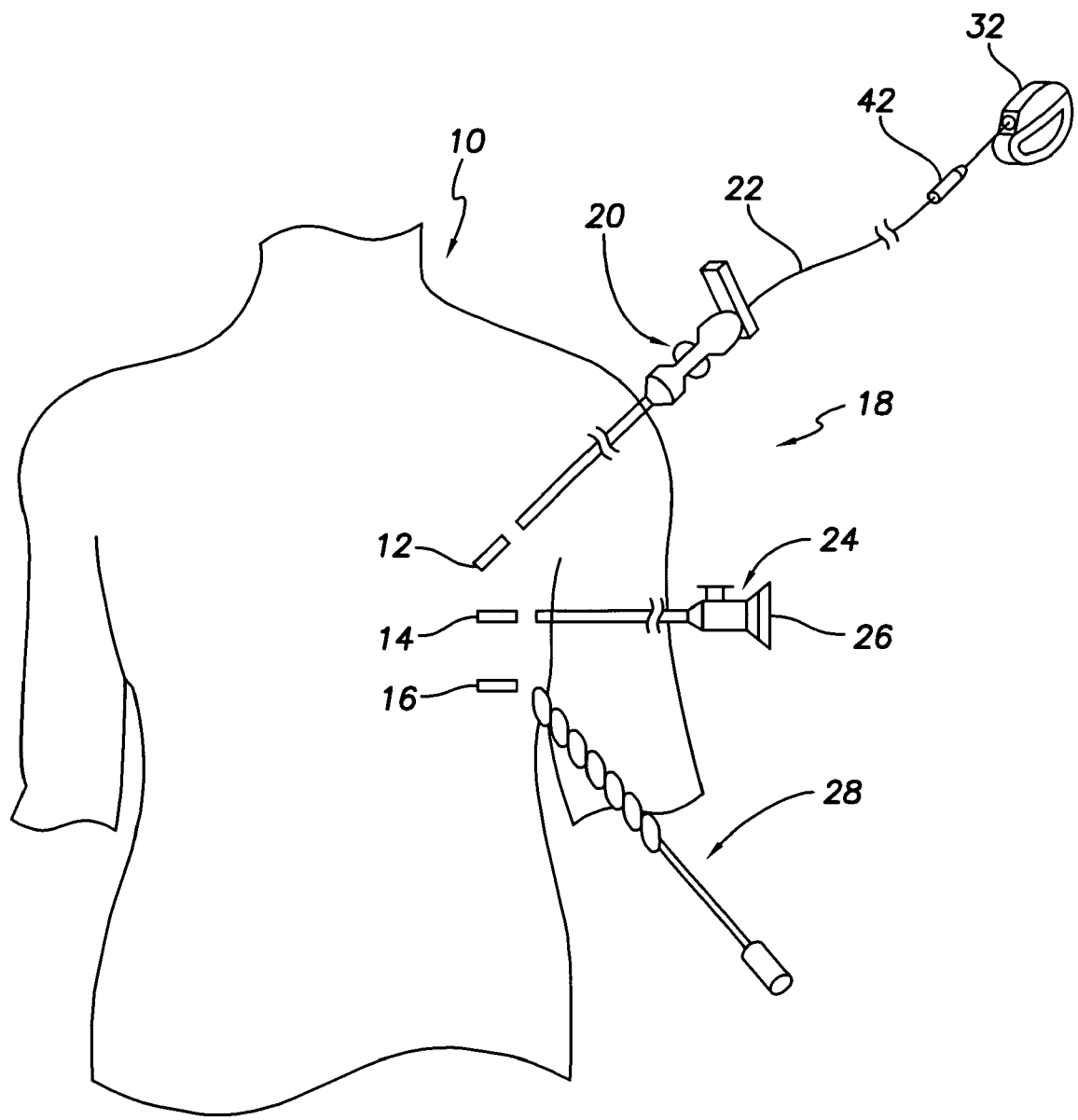
FIG. 1 is a front perspective view of the upper chest region of a human body showing in schematic form a preferred embodiment of a system for the myocardial implantation of a cardiac stimulation lead and the locations of keyhole intercostal incisions for receiving the instruments of the system.

FIG. 1 illustrates schematically a patient's upper chest region 10 having formed therein three small or keyhole intercostal incisions 12, 14 and 16 for receiving various instruments of a myocardial implantation system 18 in accordance with the present invention. Although FIG. 1 illustrates three incisions, it will be evident that two incisions or even one incision may be employed. The precise locations and sizes of the incisions and the instruments used may vary depending upon the patient's anatomy and the surgeon's preferences. Each incision may accommodate a trocar (not shown) for facilitating the insertion and manipulation of one of the instruments.

The implantation system 18 comprises an introducer 20 for inserting a myocardial cardiac stimulation lead 22 through the first incision 12 and implanting the electrode-bearing tip or header of the lead in selected cardiac tissue; a thoracoscope 24 to permit observation by the surgeon either directly through an eyepiece 26 or indirectly through an appropriate video monitor or display (not shown); and an inflatable heart jack 28 in the form of a balloon catheter (shown in its furled configuration) that can be placed underneath the heart to permit elevation of the heart within the chest cavity to provide access to regions of the heart that would not normally be available, for example, the posterior regions of the heart's left ventricle. It will be evident that the thoracoscope 24 may comprise, by way of example, a fiber optic bundle coupled to an eyepiece or display, or a CCD camera electrically connected to a display.

Figure 2:
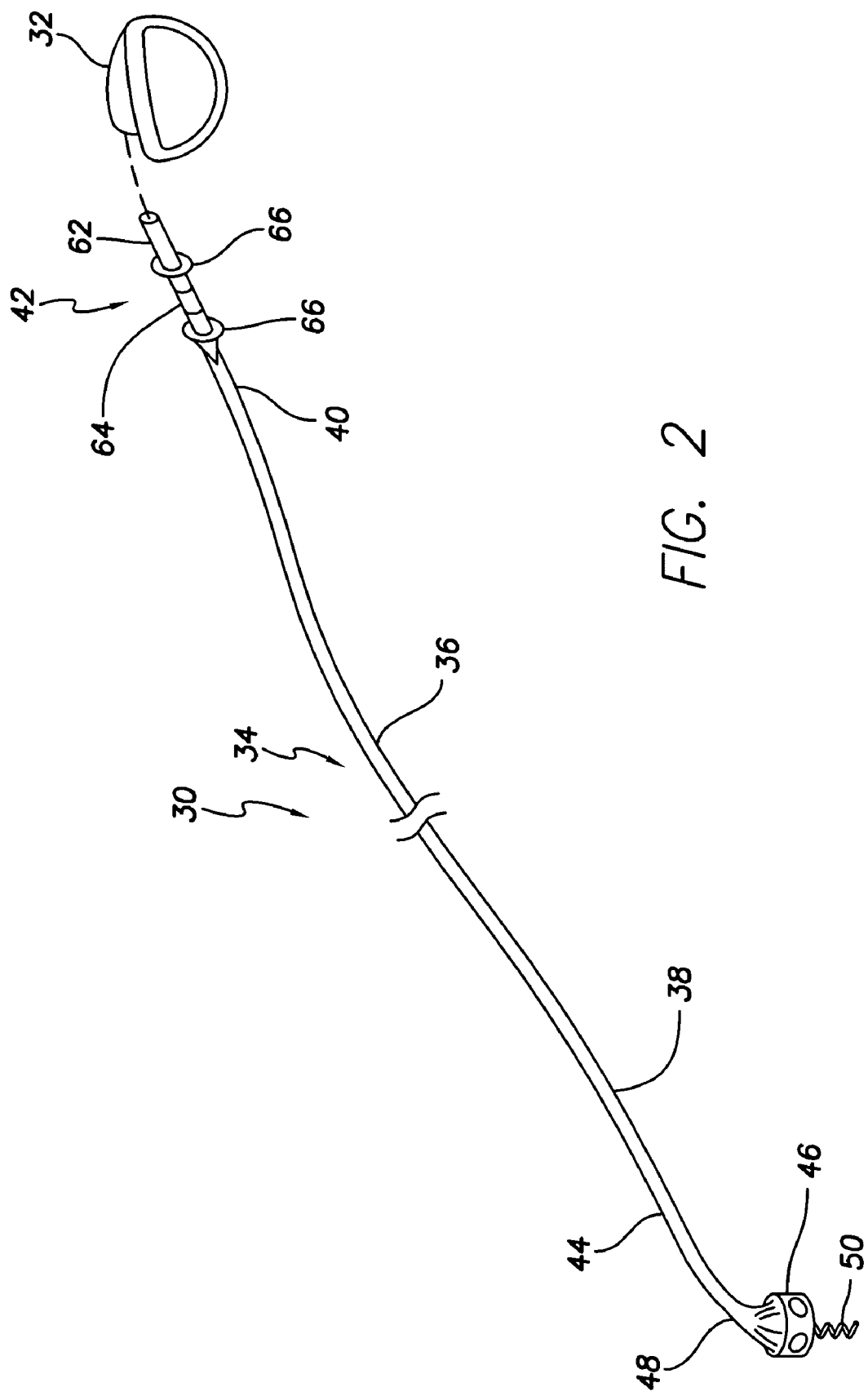
FIG. 2 is a simplified, perspective view of one embodiment of a myocardial pacing and sensing lead system that may be implanted using the instruments and techniques in accordance with the present invention.
Figure 3:
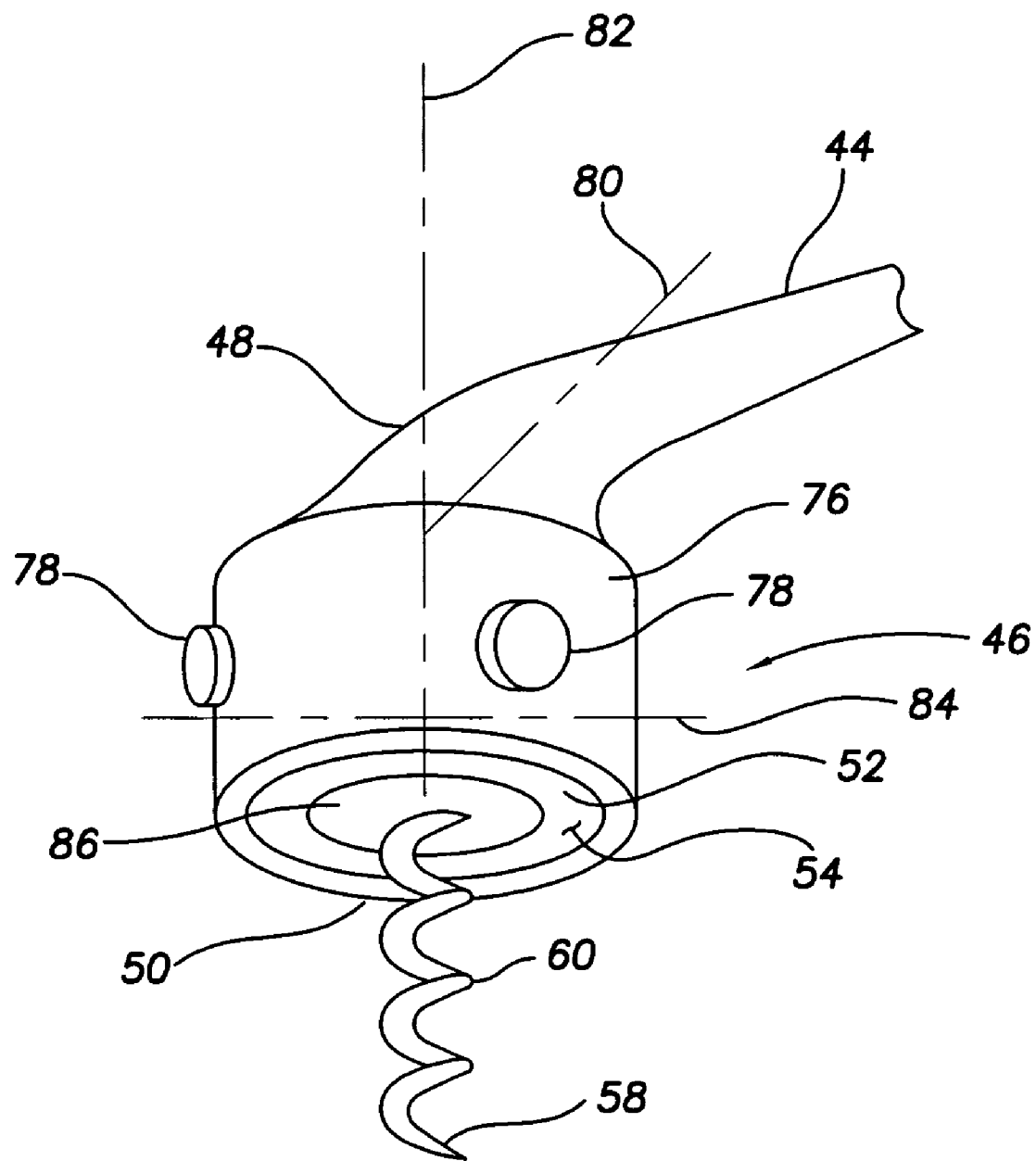
FIG. 3 is a perspective view of a preferred embodiment of an electrode header in accordance with the present invention.
Figure 4:
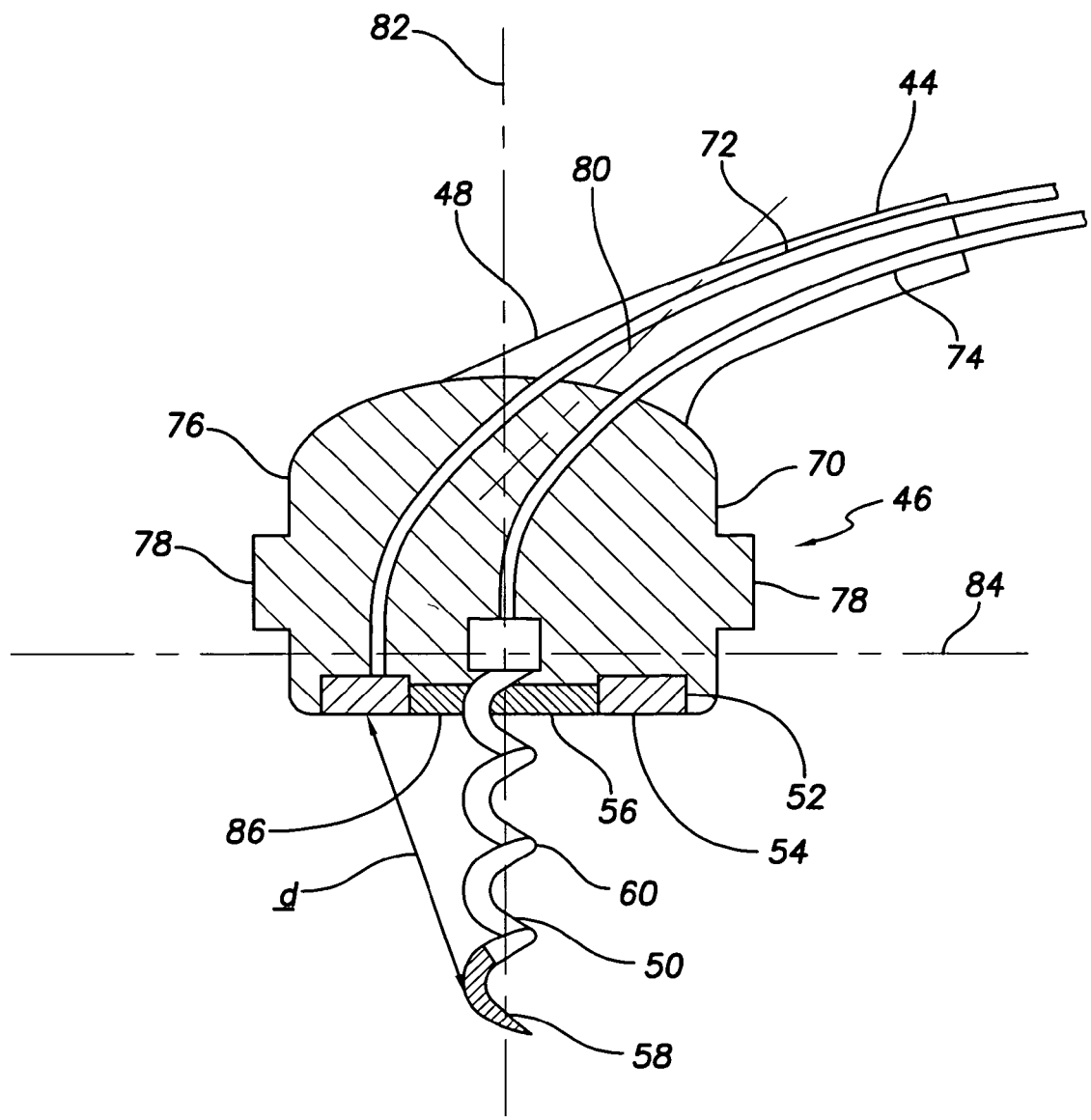
FIG. 4 is a side elevation view, in cross-section, of the electrode header of FIG. 3.
Figure 5:
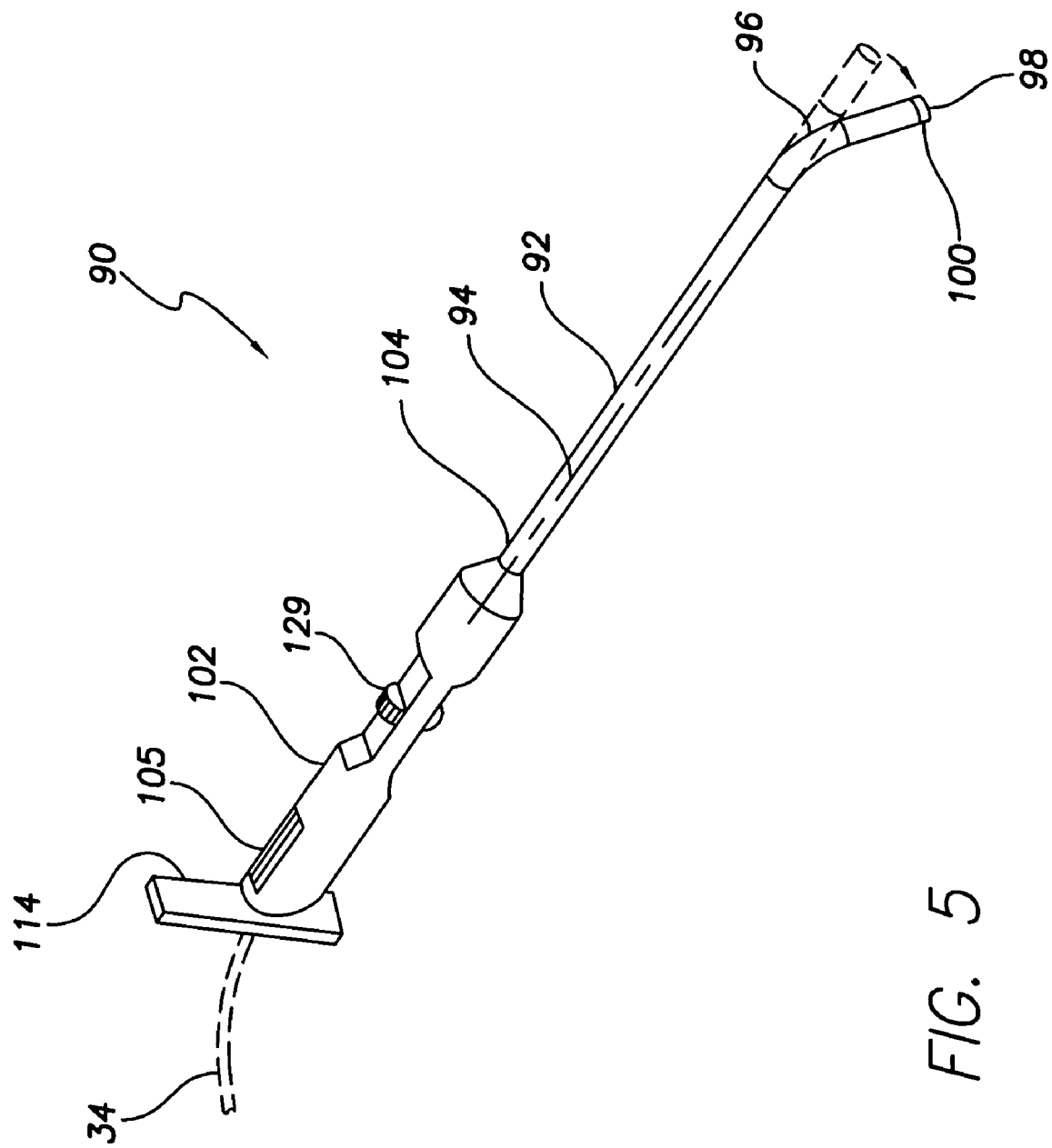
FIG. 5 is a perspective view of an introducer in accordance with one specific, exemplary embodiment of the invention for inserting and implanting the electrode header of FIGS. 3 and 4.
Figure 6:
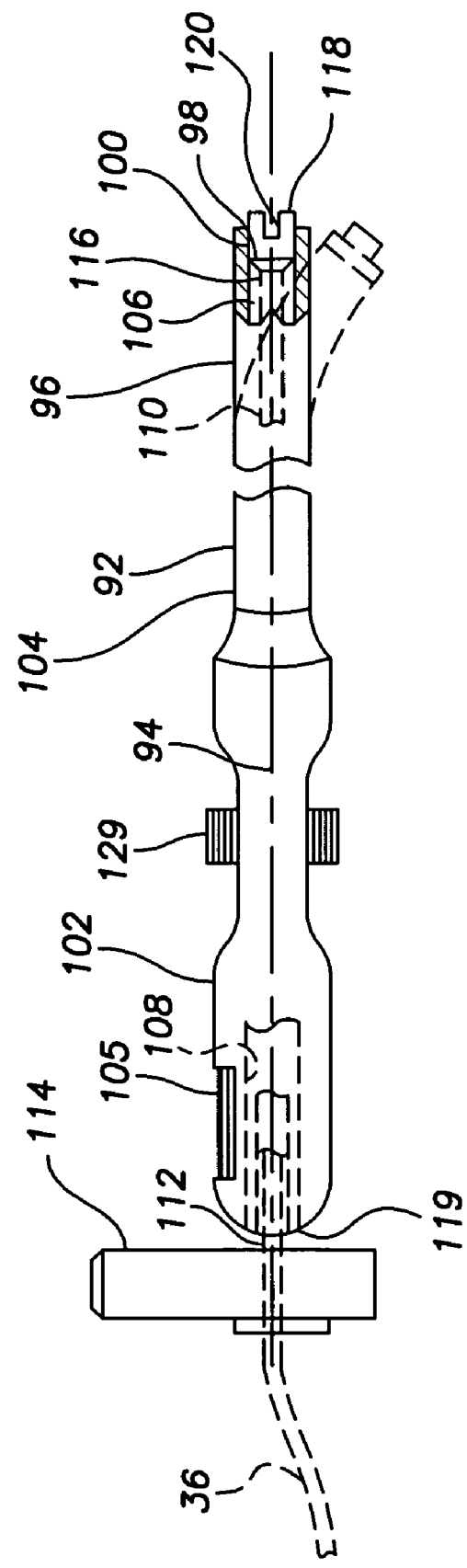
FIG. 6 is a side elevation view, partly in the cross-section, of the introducer of FIG. 5.
Figure 7:
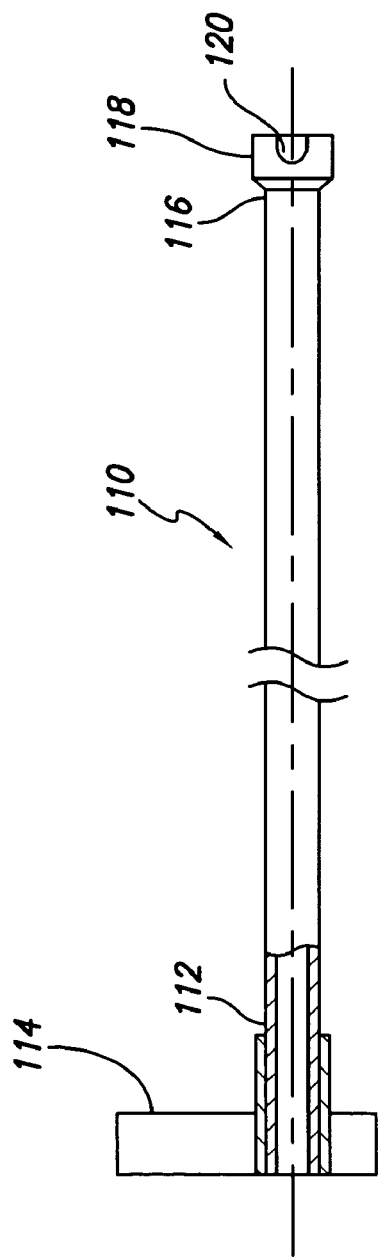
FIG. 7 is a side view, partly in the cross-section, of a driver sheath forming part of the introducer shown in FIGS. 5 and 6.
Figure 8:
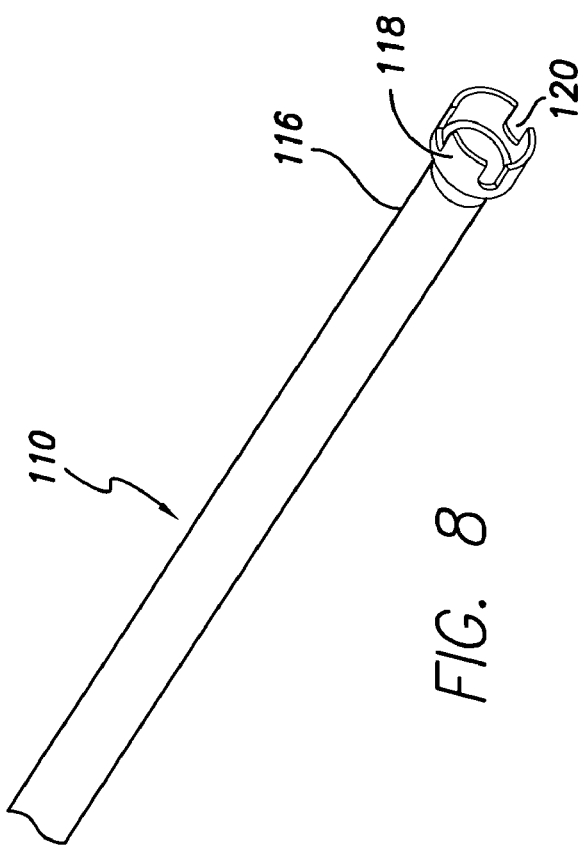
FIG. 8 is a perspective view of the distal end of the driver sheath of FIG. 7.

Referring now also to FIGS. 2-4, there is shown a specific, exemplary embodiment of an implantable lead system 30 including, generally, a cardiac pacemaker 32 and a myocardial, bipolar active fixation cardiac pacing and sensing lead 34 for connecting the pacemaker 32 with selected cardiac tissue whose electrical activity is to be stimulated and/or sensed. The lead 34 includes a lead body 36 extending along a central, longitudinal axis 38. The lead body 36 has a proximal end portion 40 carrying a connector assembly 42 for electrically connecting electrical conductors within the lead body to the pacemaker 32. The lead body further comprises a distal end portion 44 carrying at its distal extremity a bipolar, active fixation, steroid-eluting electrode header 46 that is attached to the distal extremity of the lead body at a junction 48. The header 46 comprises a helical, screw-in fixation element 50 adapted to be screwed into cardiac tissue in a manner to be described, and a ring electrode 52 concentric with the helical element 50 and having a surface 54 flush with a lower, planar surface 56 of the header. The screw-in fixation element 50 may be electrically inactive or may function as the cathode of a bipolar pacing and sensing lead system, while the ring electrode 52 typically functions as an anode. As is known, the electrically active surfaces of the cathode and anode may be coated with a material such as titanium nitride (TiN) or other suitable materials that significantly enhance the efficiency of electrode performance.

Also consistent with teachings known in the art, one or more portions of the helix electrode 50 may be electrically insulated along its length. In the example shown, only the distal tip 58 comprising, for example, about one turn of the helix electrode, is active while the remaining portion of the helix electrode is coated with an electrical insulating material 60. Whether electrically active or inactive, when advanced into the selected cardiac tissue, the helix 50 serves to stabilize or anchor the distal end portion 44 of the lead body relative to the cardiac tissue.

The connector assembly 42 carried by the proximal end portion 40 of the lead body is adapted to electrically and mechanically couple the lead body 36 to the pacemaker 32. For the embodiment under consideration, the connector assembly 42 may conform to the IS-1 standard including coaxial terminal contacts in the form of a pin terminal contact 62 and a ring terminal contact 64 positioned to engage corresponding electrical terminals within a receptacle of the pacemaker 32. To prevent ingress of body fluids into the pacemaker receptacle, the connector assembly may be provided with spaced-apart sets of seals 66. Further, in accordance with one well-known implantation technique, a stylet for delivering, steering and fixating the distal end portion 44 of the lead body during placement thereof may be inserted through a lumen in the connector pin terminal contact 62 and into a longitudinal passageway within the lead body which passageway may comprise the lumen of a coil dedicated for that purpose or also serving as an electrical conductor connecting the contact pin 62 with the helix electrode 50. As is well known, the lead body comprises a tubular housing made of a biocompatible, biostable electrically insulating material such as silicone rubber or polyurethane.

As best seen in FIGS. 3 and 4, the electrode header 46 basically comprises a header body 70 of silicone rubber or a like material molded about the proximal portions of the electrodes 50 and 52 and the electrical conductors 72 and 74 connecting the electrodes with the connector assembly 42. The header preferably has an outer, cylindrical surface 76 with a plurality of pins 78 projecting radially therefrom for engagement by the introducer in a manner to be described.

It will be noted that at the junction 48 of the lead body 36 and the header 46, the lead body extends away from the header in a direction 80 that falls between an axial direction 82 and a radial direction 84 perpendicular to the axial direction. This joinder of the distal extremity of the lead body and the header at the junction thereof is distinguishable from conventional practice wherein the lead body typically extends either along the axial direction 82 or along the radial direction 84.

The electrode header 46 preferably carries a means 86 for dispensing a steroid or other drug adjacent to the stimulation site. As is known, steroids act as anti-inflammatory agents so as to reduce the adverse reaction of the tissue to the presence of the electrodes. Preferably, the means 86 comprises a drug-permeated, monolithic controlled release device (MCRD) contained within the confines of the electrode header 46. In this fashion, a portion of the electrode header serves as the housing for the MCRD. By way of example, as seen in FIGS. 3 and 4, the MRCD may simply comprise a disk- or ring-shaped structure embedded in the header body 70 with the lower, planar surface of the disk exposed but flush with the lower planar surface 56 of the header. Other drug elution devices for use with fixation helixes appropriately soaked or otherwise impregnated with a drug to be delivered are well known in the art. The position of the drug eluting device relative to the active tip of the helix and the ring anode electrode optimizes the efficacy of the delivery of the drug.

In accordance with one specific, exemplary embodiment of the electrode header, the active surface area of the anodal ring electrode may range from 5 mm2 to 70 mm2 and the active surface area of the cathodic helix electrode may range from 2 mm2 to 15 mm2. Preferably, the anode to cathode active surface area ratio may be 1.5 to 1, or greater. In accordance with one preferred example, the anodal ring electrode may have an active surface area of 15 mm2 and the cathodic helix electrode may have an active surface area of 5 mm2 for an anode to cathode active surface area ratio of 3 to 1. In addition, with reference to FIG. 4, the distance d between the electrically active portion 58 of the helix 50 and the electrically active surface 54 of the anode 52 is preferably at least 1 mm, but preferably no more than about 10 mm.

FIGS. 5-12 show a steerable introducer 90 in accordance with one embodiment of the invention. The introducer 90 comprises an elongated tubular outer sheath or body 92 extending along a longitudinal, central axis 94. The outer introducer body 92 may be fabricated of any suitable biostable, biocompatible material. The tubular outer body 92 of the introducer includes a flexible, deflectable distal end section 96 terminating at a distal tip 98 that preferably includes a mapping electrode 100 that preferably may take the form of a ring, but may also take the form of any convenient geometric shape compatible with the introducer 90. The outer body 92 may have various lengths; in accordance with one specific, exemplary form of the introducer, the length of the outer body 92 may range from 6 to 20 inches, and may have a preferred length of 15 inches. The distal end section 96 of the outer introducer body 92 may comprise a short section that is more flexible than the remainder of the body 92. A directional actuator is provided for deflecting the flexible distal end section 96. In accordance with one embodiment of the invention, the directional actuator includes a control hand grip 102 attached to a proximal end 104 of the introducer body. Mounted on a proximal portion of the introducer grip 102 is a terminal 105 that may simply comprise an elongated, wire-like element seated in a recess formed in the grip. Thus, the terminal may be accessed by a connector such as an alligator clip that in turn may be connected by an electrical cable to an instrument, such as a voltmeter or a pacing system analyzer (PSA), for displaying the sensed electrical activity of the myocardium.

Figure 10:
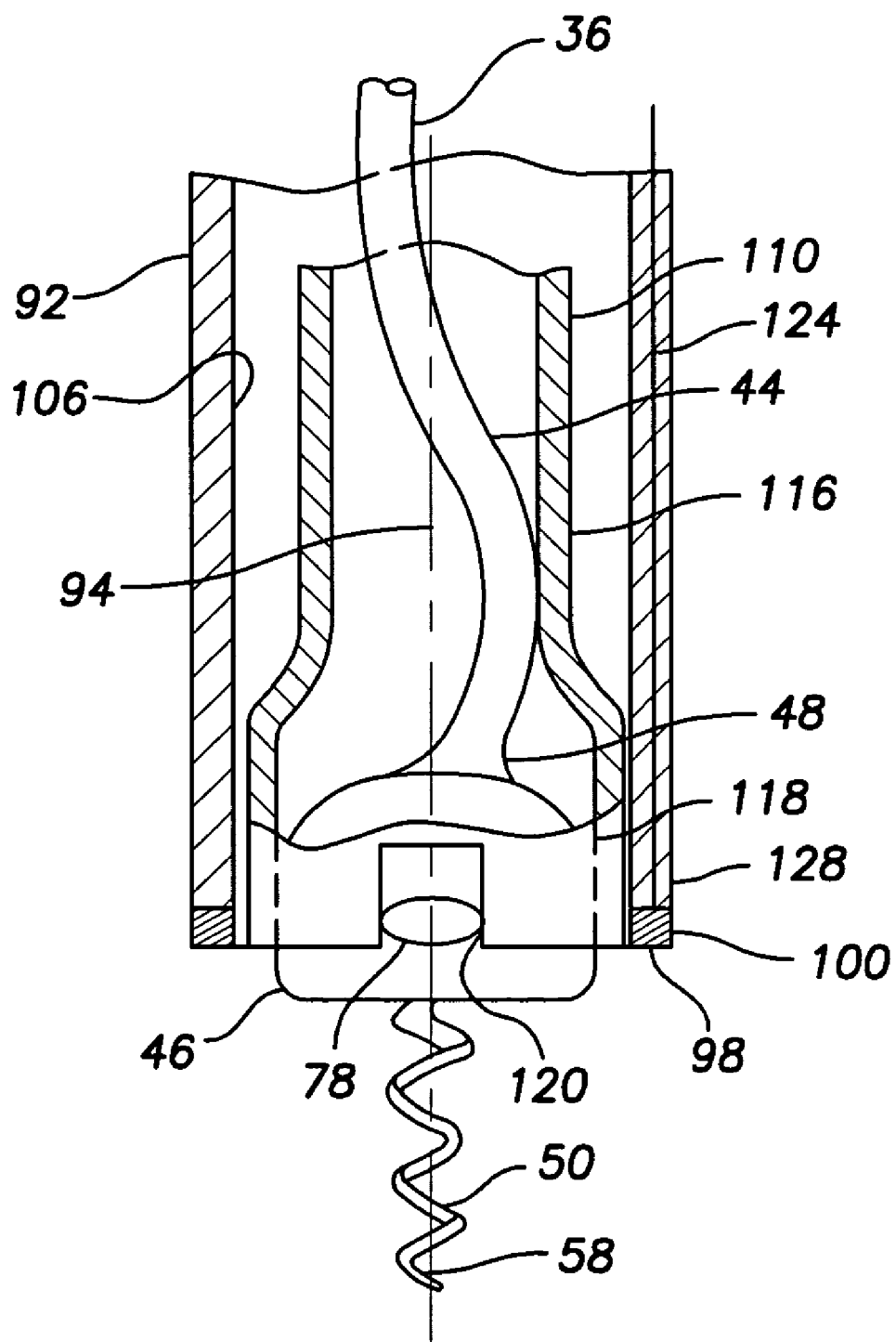
FIGS. 10 and 11 are side views, partly in cross-section, of the distal end of the introducer of FIGS. 5-9 showing an electrode header such as that depicted in FIGS. 2-4 in place within the introducer.

The tubular body 92 defines a central lumen 106 coextensive with a lumen 108 in the grip 102, for receiving a flexible, inner tubular sheath 110 that, when inserted in the introducer body 92, has a projecting proximal end 112 carrying a radially extending handle 114 and a distal end 116 comprising an enlarged electrode header driver 118 that may partially project from the distal tip 98 of the outer tubular introducer body. The inner tubular sheath 110 is displaceable both rotationally and longitudinally relative to the body 92 and may be completely pulled out of the introducer through a proximal end 119 of the grip 102. When fully inserted, the handle 114 engages the proximal end 119 of the introducer grip 102. The lead 34 is inserted into the inner sheath 110, connector end first, through the enlarged header driver 118 and pulled through until the pins 78 projecting from the side of the electrode header 46 are received by and seated within longitudinally extending slots 120 formed in the tubular header driver 118, as best seen in FIG. 10. It will thus be appreciated that rotation of the handle 114 relative to the hand grip 102 rotates the electrode header driver 118 and the electrode header 46 engaged thereby, thereby permitting the helix electrode 50 to be screwed into the myocardium upon rotation, typically clockwise, of the handle 114.

It will be evident that the driving connection between the header driver 118 and the header 46 may be provided by configured, matable surfaces other than the projecting pins 78 and the associated slots 120. For example, one or more flats may be provided on the interior surface of the header driver 118 with a correspondingly configured outer surface on the electrode header 46. Tongue and groove or spline couplings are further examples of what may be used.

Figure 11:
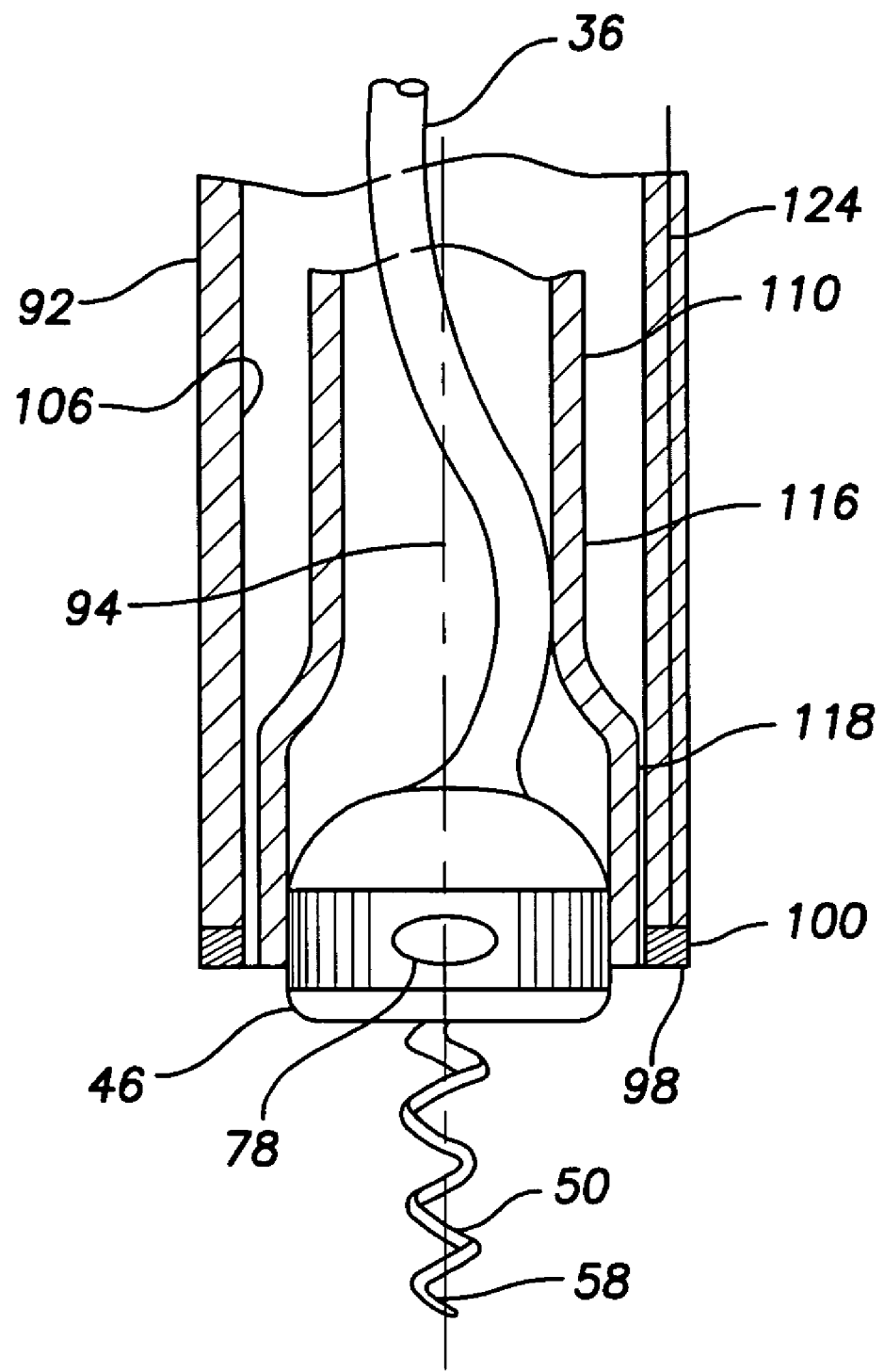

The introducer 90 further includes at least one elongated actuation member 124 that may comprise a pull wire or cable, preferably electrically conductive, extending from the hand grip 102 through a longitudinally-extending passageway in the wall of the outer tubular introducer body 92 to a distal extremity 128 attached to the mapping electrode 100 so as to be anchored at an off-axis point within the flexible distal end section 96 of the introducer body. (FIGS. 10-12.)

The use of a single actuation member in the form of the pull cable 124 will cause deflection of the flexible distal end section 96 of the introducer in one direction (against the tendency of the section 96 to assume its normally straight configuration) when the proximal end of the cable is pulled in a proximal direction. Such a single bending direction may be sufficient for most purposes for manipulating the header 46 and effecting its implantation in the cardiac tissue upon rotation of the handle. It will be evident, however, that more than one pull wire or cable may be employed with each cable being anchored to the introducer body at off-axis points located proximally of the tip. The anchoring points may lie along a common transverse plane or, alternatively, they may be anchored at different, axially spaced-apart points to allow for compound deflections of varying curvatures in the flexible distal end section 96 of the outer introducer body 92 to enhance the ability to quickly steer the distal end section 96 of the outer introducer body and the inner sheath 110 carried thereby to the target location.

It will be appreciated that by placing the lead body 36 inside the tubular structure of the introducer, wrapping of the lead about the exterior of the introducer, a common problem with currently available myocardial lead introducer systems, is avoided.

Figure 12:
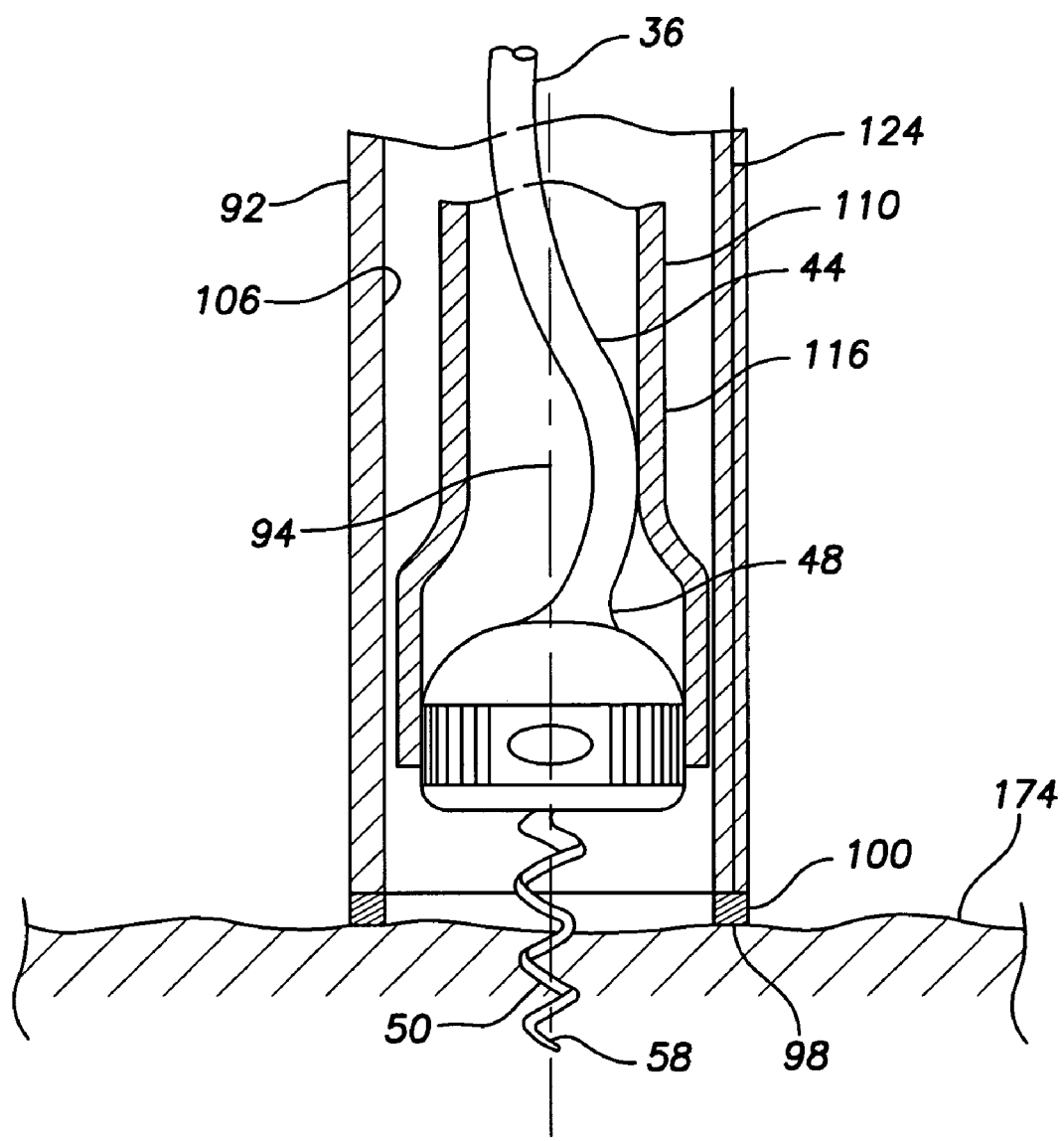
FIG. 12 is further to FIGS. 10 and 11, showing the helical electrode carried by the electrode header screwed partway into the heart and the distal tip of the introducer positioned to engage the surface of the heart for mapping purposes.

FIG. 12 shows the introducer in its mapping configuration in which the outer introducer body 92 has been advanced relative to the inner driver sheath 110 so that the mapping electrode 100 may be brought into contact with a surface 174 of the heart and moved therealong to locate an optimal point for implantation of the helix electrode 50 following which the inner sheath is advanced relative to the outer body and rotated to screw the helix electrode 50 into the heart tissue. FIGS. 10-12 also show how the distal end portion 44 of the lead body is gently curved inside the inner sheath 110 adjacent to the header/lead body junction 48, to minimize stress at the junction.

Figure 9:
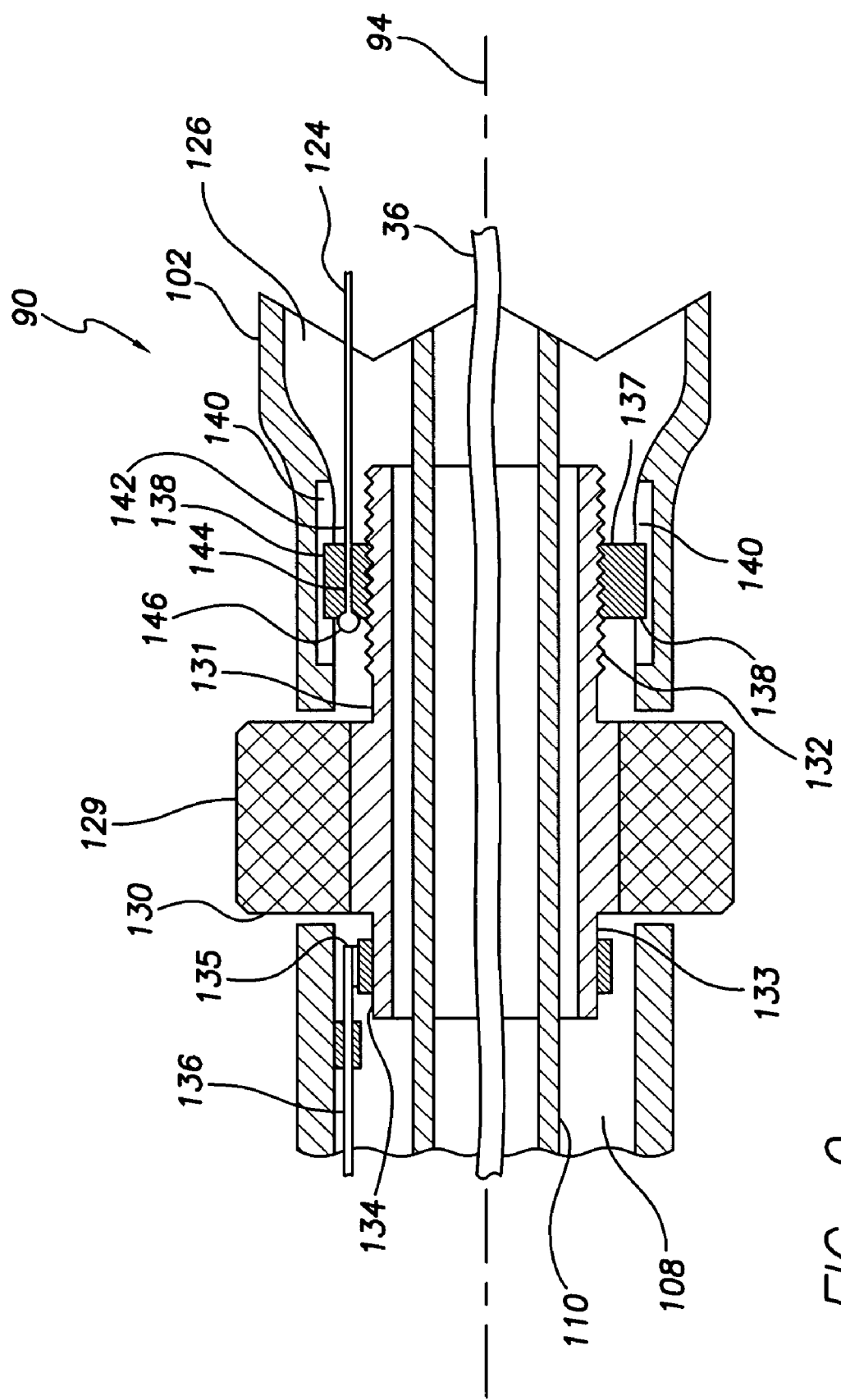
FIG. 9 is an axial cross-section of a portion of the introducer of FIGS. 5 and 6.

Turning now to FIG. 9, longitudinal movement of the single actuating member 124 may be effected by a knurled, rotatable thumbwheel 129 carried by the control hand grip 102. In the embodiment of FIG. 9, the thumbwheel 129 is rotatable about the central, longitudinal axis 94 of the introducer. The thumbwheel 129 comprises an outer, insulative ring 130 and an inner, electrically conductive sleeve 131 bonded to the outer ring 130 so as to be rotatable therewith. The sleeve 131 comprises an externally threaded, distally projecting extension 132 and a proximally projecting extension 133 carrying an electrically conductive contact ring 134. An electrical contact 135, biased into slidable engagement with the ring 134 is mounted on the distal end of an electrical conductor connected to the terminal 105.

Mounted on the threaded extension 132 is an electrically conductive traveling nut 137 that moves longitudinally in response to rotation of the thumbwheel. The traveling nut 137 is restrained against rotation by outer projections 138 thereon each extending into a longitudinally extending groove 140 formed in the inner wall of the tubular, outer introducer body 92. A proximal end 142 of the electrically conductive pull wire 124 extends through an axial aperture 144 in the traveling nut; the pull cable has an enlarged end 146 for anchoring the cable. Thus, advancement or retraction of the traveling nut 137 in response to rotation of the thumbwheel 129 deflects (or allows re-straightening of) the flexible distal end section 96 of the introducer body 92 to facilitate guidance and steering of the distal end section 96 around obstructions and ultimately to the target location on the myocardium. In addition, it will be appreciated that electrical continuity is established between the mapping electrode 100 and the terminal 105 via the pull wire 124, the traveling nut 137, the sleeve 131, the contact elements 134 and 135, and the conductor 136. It will also be understood that a non-mapping embodiment may be provided by eliminating the mapping electrode 100 and simply anchoring the distal end of the actuating member 124 (which then need not be electrically conductive) at an off-center point within the distal tip of the introducer body 92.

Figure 13:
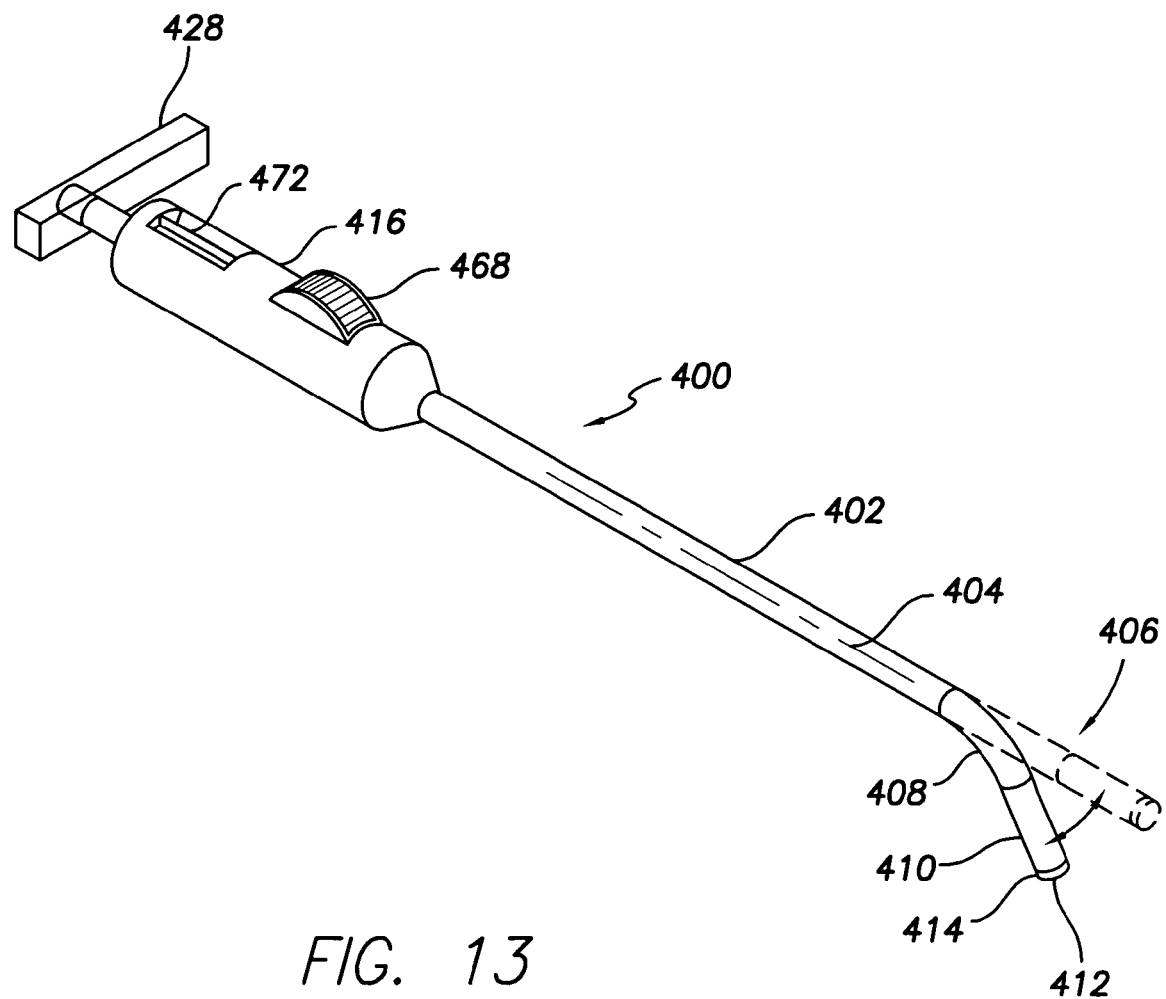
FIG. 13 is a perspective view of a steerable introducer in accordance with an alternative embodiment of the invention.
Figure 14:
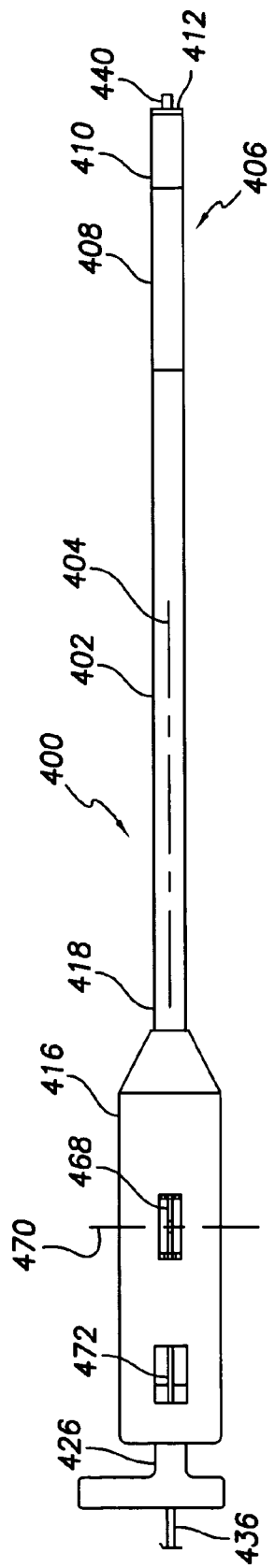
FIG. 14 is a top plan view of the introducer of FIG. 13.
Figure 15:
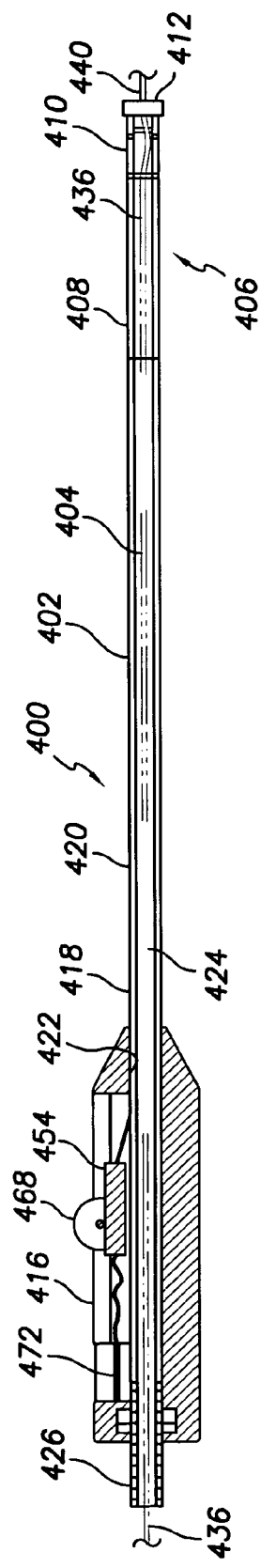
FIG. 15 is a side view, in cross section, of the introducer of FIG. 13.
Figure 20:
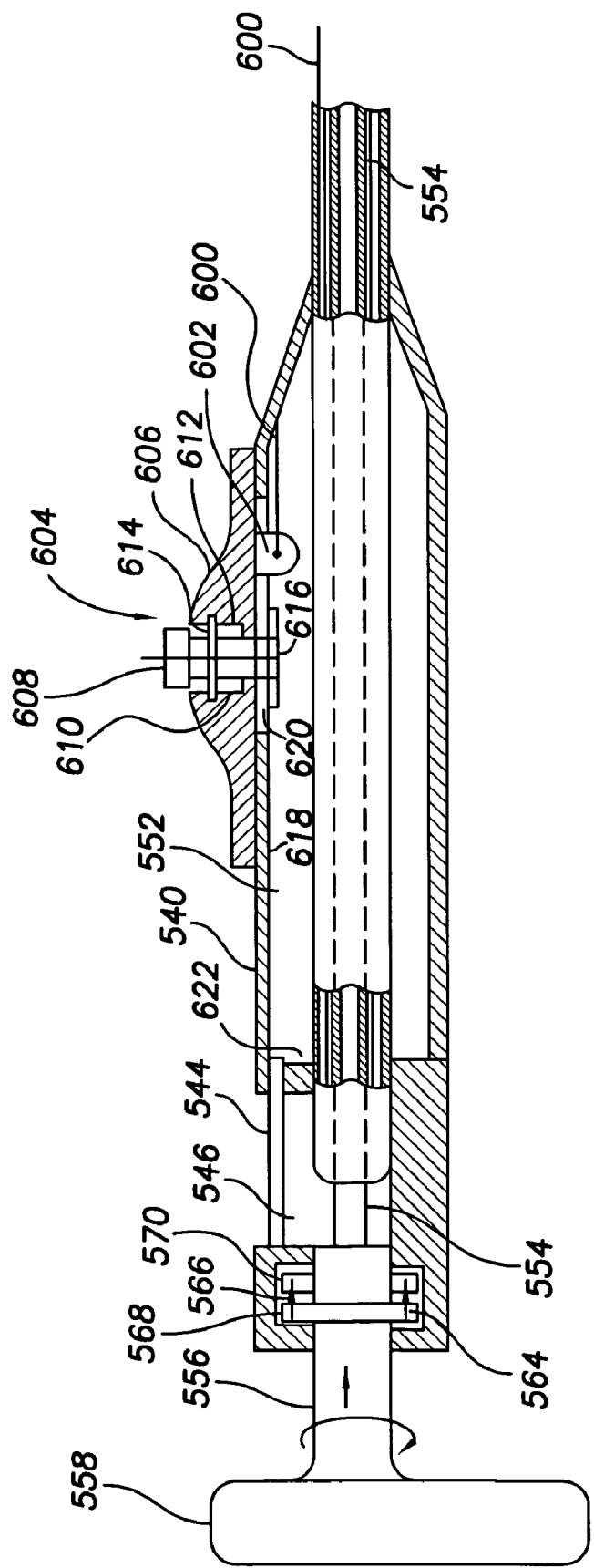
FIG. 20 is a side elevation view, in cross section, of a handgrip forming part of the steerable introducer shown in FIGS. 18 and 19.
Figure 21:
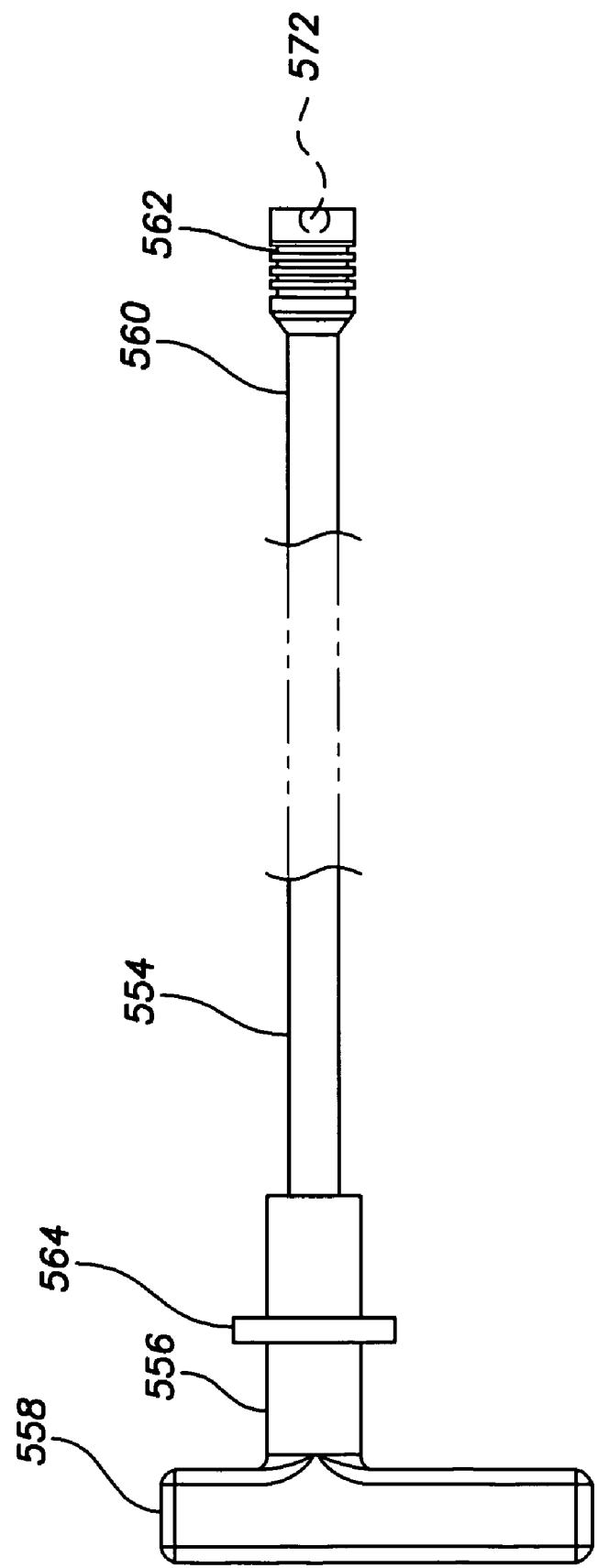
FIG. 21 is a side elevation view of an inner sheath forming part of the steerable introducer of FIGS. 18 and 19.

FIGS. 13-17 show a steerable introducer 400 in accordance with another specific exemplary embodiment of the invention. The introducer 400 comprises an elongated, outer sheath or body 402 extending along a longitudinal, central axis 404. The outer introducer body 402 comprises a generally tubular structure fabricated of any suitable biostable, biocompatible material. The tubular introducer body 402 includes a deflectable distal end portion 406 comprising a flexible section 408 and a stiff section 410 at the distal extremity of the introducer body. The stiff section 410 terminates at a distal tip 412 that preferably includes a mapping electrode 414 that may take the form of a electrically conductive ring. As before, the outer tubular body 402 may have various lengths and in accordance with one, specific exemplary form thereof the length may be about 15 inches. In the absence of an applied deflecting force, the distal end portion 406 of the introducer body 402 assumes a straight configuration as shown in FIGS. 13-15. The flexible section 408 of the distal end portion thus serves to restore the distal end portion 406 to its normally straight configuration upon removal of a deflecting force.

A directional actuator is provided for deflecting the distal end portion. The directional actuator comprises a control handgrip 416 attached to a proximal end 418 of the introducer body 402. The tubular body 402 defines a central lumen 420 co-extensive with a lumen 422 in the handgrip 416 for receiving a flexible, inner tubular sheath 424, that, when inserted in the introducer body, has a projecting proximal end 426 carrying a radially extending handle 428 and a distal end 430 comprising an enlarged electrode header driver 432. The tubular sheath 424 is displaceable within the outer introducer body 402 both rotationally and longitudinally relative to the introducer body and may be completely pulled out of the introducer through a proximal end 434 of the handgrip. A lead body 436 is inserted into the inner sheath 424, connector end first, through the enlarged header driver 432 and pulled through until an electrode header 438 on the distal tip of the lead 436 engages the tubular header driver 432. Accordingly, rotation of the handle 428 relative to the handgrip 416 rotates the electrode header driver 432 and the electrode header 438 engaged thereby, thus permitting a helix electrode 440 to be screwed into the myocardium upon rotation, typically clockwise, of the handle 428. As already explained in connection with the first embodiment, the driving connection between the header driver and the header may be provided by appropriately configured, matable surfaces such as projecting pins and associated slots, and so forth.

The introducer 400 further includes at least one elongated actuation member 450 preferably comprising a pull wire or cable, preferably electrically conductive, attached at a proximal end 452 thereof to a longitudinally movable block 454 within the handgrip 416 and a distal end 456 (FIG. 17) secured to the mapping electrode 414 and, accordingly, off center relative to the central axis. Except for a proximal portion 458 within the handgrip 416, the electrically conductive pull wire 450 is contained within a longitudinally extending passageway 460 formed in the wall of the introducer body 402. Formed in an upper surface 462 of the pull wire block 454 is a rack gear 464 in mesh with a pinion 466 mounted on a thumbwheel 468 rotatable about an axis 470 transverse of the longitudinal axis 404 of the introducer body. It will thus be seen that counter clockwise rotation (as seen in FIGS. 15 and 16) of the thumbwheel will cause retraction of the block 454 and the pull wire 450 attached thereto so as to deflect the distal end portion 406 of the introducer body and the inner sheath 424 contained therein.

The pull wire block 454 is preferably electrically conductive and is connected to a mapping electrode terminal 472 by means of a flexible conductor cable 474 electrically connecting the terminal 472 with a proximal end 476 of the pull wire block 454. As in the first embodiment, the terminal 472 is adapted to receive a connector such as an alligator clip to provide an electrical signal path from the mapping electrode 414 to a measuring instrument such as a voltmeter or a PSA via the electrically conductive pull wire 450, block 454, flexible conductor 474 and terminal 472.

The embodiment shown in FIGS. 13-17 provides for the deflection of the flexible distal end portion 406 of the introducer 400 in one direction in response to rotation of the thumbwheel 468. Releasing the thumbwheel permits the distal end portion of the introducer body to return to its normal, straight position causing the block to move to its original, rest position. As explained in connection with the first embodiment, additional pull wires may be employed to provide for multi-directional deflections of the distal end portion of the introducer body, and a non-mapping embodiment may be provided by eliminating the mapping electrode 414, the terminal 472 and the conductor cable 474.

Figure 22:
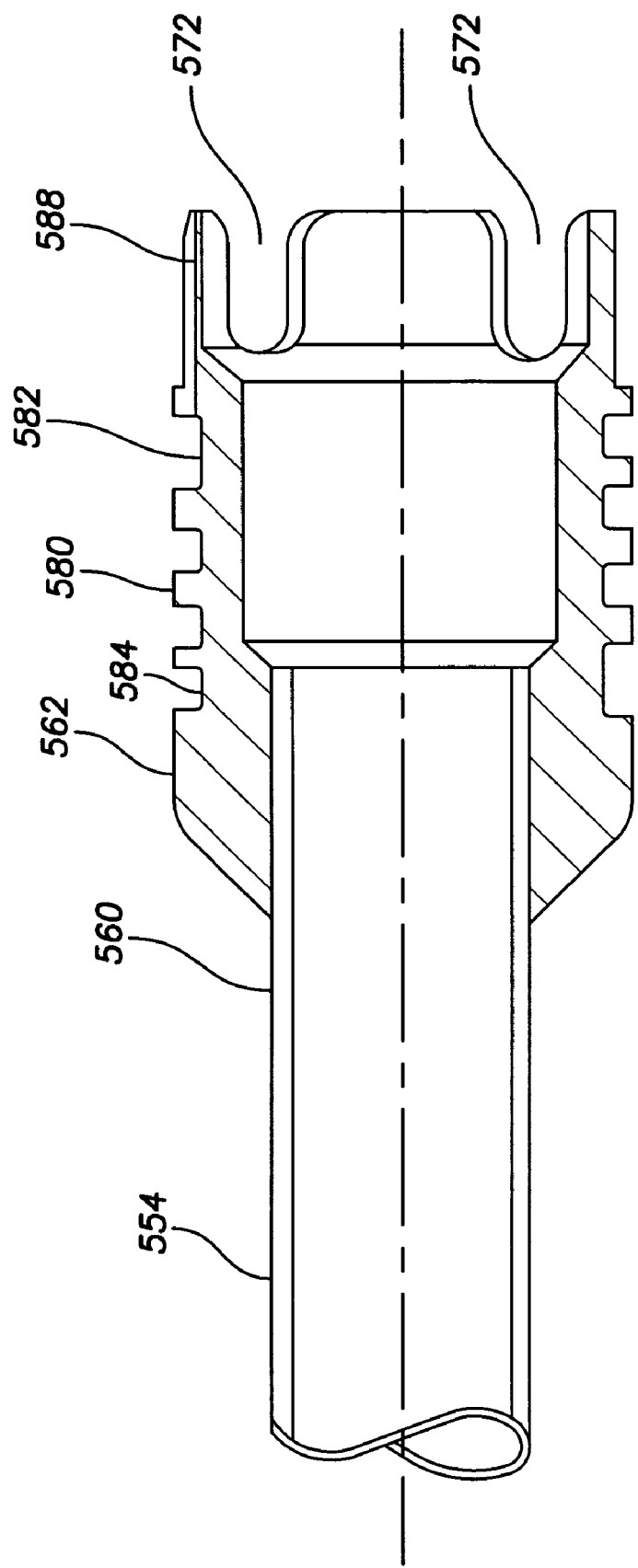
FIG. 22 is an enlarged side elevation view, in cross section, of an electrode header driver attached to the distal end of the inner sheath of FIG. 21.
Figure 23:
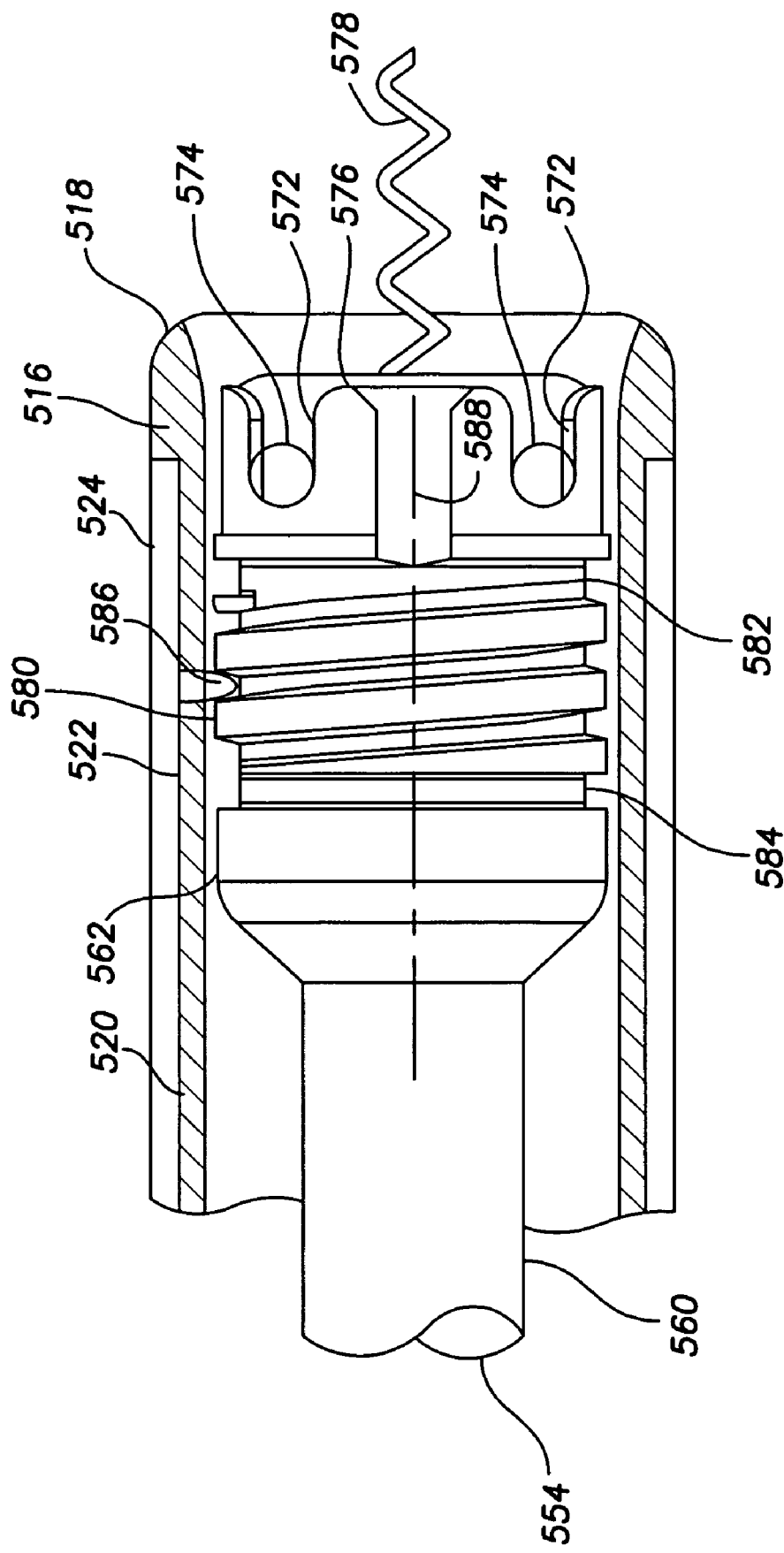
FIG. 23 is an enlarged side elevation view, partly in cross section, of the distal end of the steerable introducer of FIGS. 18 and 19.
Figure 24:
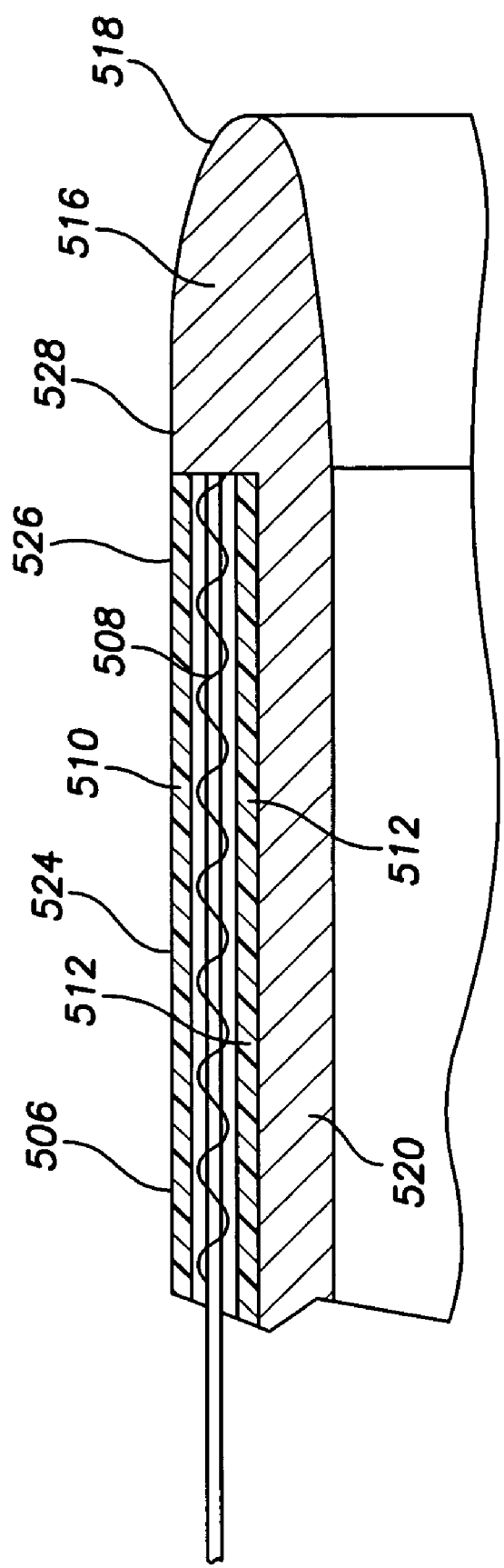
FIG. 24 is an enlarged side elevation view, in cross section, of a portion of a mapping electrode at the distal end of the steerable introducer of FIGS. 18 and 19.

FIGS. 18-25 show a steerable introducer 500 in accordance with yet another embodiment for implanting a lead 501. The introducer 500 comprises an elongated outer body or sheath 502 extending along a longitudinal, central axis 504. The outer introducer sheath 502 comprises a flexible tubular wall 506 that may be fabricated of any suitable biostable, biocompatible material; however, the sheath wall 506 preferably comprises a 3-ply structure including an inner layer 508 comprising a flexible, electrically conductive wire mesh sandwiched between a pair of insulating, polymer layers 510 and 512. (FIG. 24) The outer sheath 502 includes a distal end section 514 carrying a tubular mapping electrode 516 having a blunt or rounded distal tip 518 for engaging the body tissue whose electrical potentials are to be mapped. The mapping electrode 516 has a proximal portion 520 having a recess 522 for receiving a distal end 524 of the outer sheath wall 506, so that an outer surface 526 of the wall 506 is flush with an outer surface 528 of the distal tip 518 of the mapping electrode (FIGS. 23 and 24). The outer sheath may have various lengths; in accordance with one specific, exemplary form of the introducer, the length of the outer sheath may range, for example, from 6 to 20 inches, with a preferred length of about 15 inches.

Figure 25:
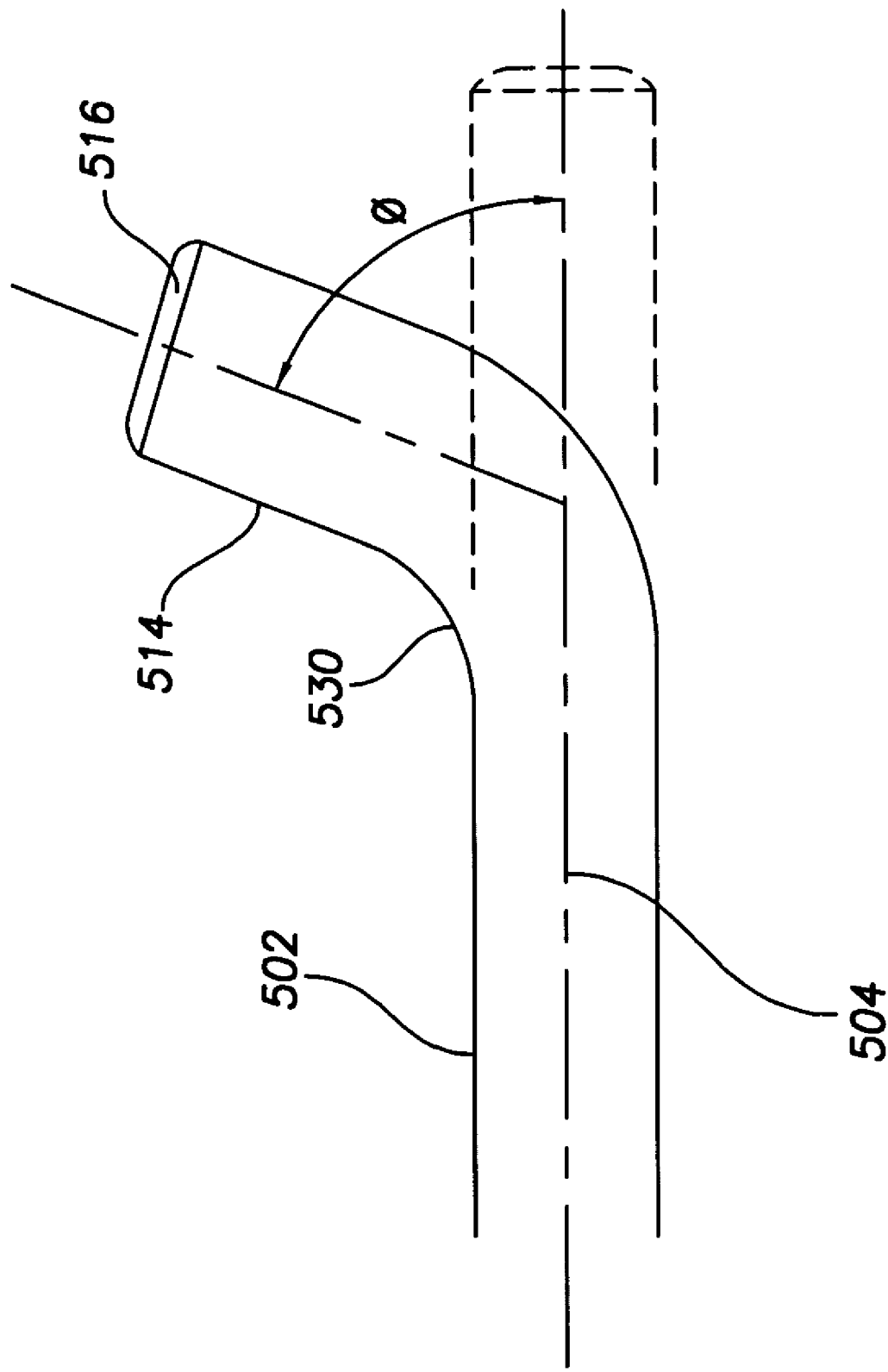
FIG. 25 is a side elevation view of a deflectable distal end section of the steerable introducer of FIGS. 18 and 19.

The distal end section 514 of the outer introducer sheath 502 may comprise a short section 530 proximal of the tubular mapping electrode 516 that is more flexible than the remainder of the sheath (FIG. 25). A directional actuator is provided for deflecting the flexible distal end section 514 through an angle θ preferably of, for example, up to 75°, but that may have a range extending up to 135° (FIG. 25). Preferably, the directional actuator includes a control handgrip 540 attached to a proximal end of the introducer sheath 502. Mounted on a proximal portion of the handgrip 540 is an electrical terminal 544 that may comprise an elongated, wire-like element seated in a recess formed in the grip 540. The terminal 544 may be thus accessed by a connector such as an alligator clip that in turn may be coupled to an instrument such as a voltmeter or a PSA for displaying the sensed electrical activity of the target body tissue such as the myocardium.

The tubular sheath 502 defines a central lumen 550, coaxial with a lumen in the handgrip 540, for receiving a flexible, inner tubular sheath 554 that has a proximal end 556 carrying a radially extending handle 558 and a distal end 560 carrying an electrode header driver 562 generally along the lines previously described.

Projecting radially outwardly from the proximal end of the inner sheath 554 is a flange 564 contained within a cylindrical cavity 566 formed in the proximal end of the handgrip 540. The inner tubular sheath 554 is displaceable both rotationally and longitudinally relative to the outer sheath 502 with the extent of the inner sheath's longitudinal displacement being constrained by spaced-apart end walls 568 and 570 of the cylindrical cavity 566 which walls are engageable by the flange 564 at the limits of the inner sheath's longitudinal travel. Separation of the sheaths 502 and 554 from each other is thereby also prevented.

As in the previously described embodiments, the electrode header driver 562 at the distal end of the inner tubular sheath 554 defines cutouts 572 for engaging corresponding lugs 574 projecting from the outer surface of an electrode header 576 of a lead inserted into the inner tubular sheath 554. The electrode header 576 carries a fixating helix 578 that may be screwed into body tissue such as the myocardium. In the present embodiment, the driver 562 has an outer surface carrying threads 580 whose pitch preferably matches that of the fixating helix 578. The distal end of the threads 580 terminate at, and communicate with, a distal annular channel 582. Similarly, the proximal end of the threads 580 terminate at, and communicate with, a proximal annular channel 584. The distal end of the outer introducer sheath 502 carries an inwardly extending thread guide pin 586 that projects into the threads 580 on the electrode header driver. Thus, with the guide pin 586 in engagement with the threads 580 on the header driver, rotation of the handle 558 advances or retracts the driver 562 and the electrode header 576 carried thereby. When the guide pin is in either of the end annular channels 582, 584 the driving sheath 554 is free to rotate without advancement or retraction thereof. The longitudinal distance separating the annular channels 582 and 584 is such that when the guide pin 586 is in the proximal channel 584, the distal end surface of the driver 562 is approximately flush with the distal tip of the outer sheath 502 and the helix 578 is fully extended from the distal tip. Conversely, when the guide pin 586 is in the distal channel 582, the helix 578 is fully retracted within the distal tip of the introducer sheath 502.

As seen in FIGS. 22 and 23, the outer surface of the header driver 562 includes a longitudinally extending channel 588 connecting the distal tip of the driver with the distal annular channel 582. During assembly of the inner and outer sheaths 502 and 554, the inner sheath is advanced within the outer sheath and rotated to bring the guide pin 586 into alignment with the longitudinal channel 588. Advancement of the inner sheath 554 causes the guide pin 586 to enter the distal annular channel 582. Such assembly is effected by constructing the handgrip 540 so as to be separable along a central, vertical longitudinal plane. Separating the split structure of the control handgrip permits the flange 564 to be placed inside the cylindrical cavity 566 following which the handgrip halves are joined by appropriate fasteners or a bonding agent.

The introducer 500 further includes at least one elongated deflection actuator member 600 that may comprise a pull wire or cable, preferably electrically conductive, extending from the mapping electrode 516 tip to a lug 602 depending from a manually operable, longitudinally displaceable slide 604 on the control handgrip 540. The pull wire or cable 600 extends along the length of the outer sheath, preferably within the inner wire mesh layer 508 of the wall 506. The use of a single actuation member in the form of a pull wire or cable will cause deflection of the flexible distal end section 514 of the introducer in one direction against the tendency of the end section to assume its normally straight configuration when the proximal end of the wire or cable 600 is pulled in a proximal direction. As noted earlier, such a single bending direction may be sufficient for most purposes for manipulating the electrode header and effecting its implantation in the cardiac tissue upon rotation of the handle 558 of the inner sheath. It will be evident, however, that more than one pull wire or cable may be employed with each cable being anchored to the mapping electrode tip at off-axis points. The various anchoring point arrangements described in connection with previous embodiments may be utilized to allow, for example, for compound deflections of varying curvatures so as to enhance the ability to quickly steer the distal end section 514 of the outer introducer sheath 502 and the inner sheath 554 carried thereby to a target location. As before, it will be appreciated that by placing the lead body inside the tubular structure of the introducer, wrapping of the lead about the exterior of the introducer is avoided.

The slide 604 on the handgrip comprises a body portion 606 carrying a spring-loaded push button 608 biased outwardly by means of a compression spring 610 captured between a lower wall 612 of the slide body and an outwardly extending flange 614 affixed to the push button. Attached to a lower extremity of the push button 608 is a friction plate or shoe 616 that normally engages an inner surface 618 of the wall of the handgrip. Depression of the push button 608 disengages the shoe 616 from the surface 618 allowing the slide 604 to be displaced longitudinally, with the push button 608 and depending lug 602 being free to travel within a longitudinal slot 620 formed in the wall of the handgrip.

The mapping electrode terminal 544 carried by the handgrip is electrically connected to the electrically conductive wire mesh 508 by means of an electrical conductor 622. Thus, it will be seen that electrical continuity is established between the mapping electrode and the mapping electrode terminal by means of the electrically conductive mesh.

Figure 26:
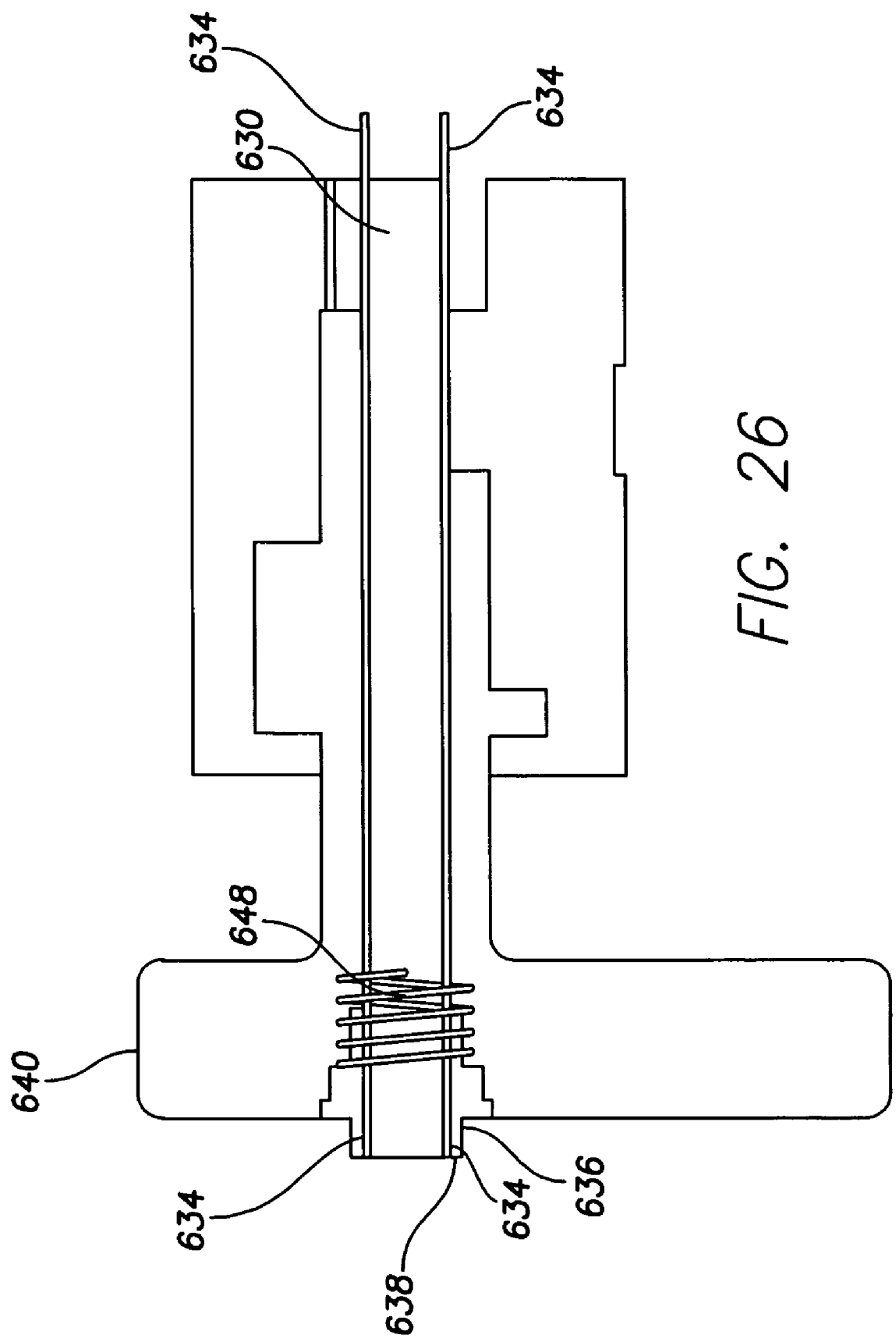
FIG. 26 is a side elevation view, in cross section, of the proximal end portion of a steerable introducer in accordance with yet another exemplary embodiment of the present invention.
Figure 27:
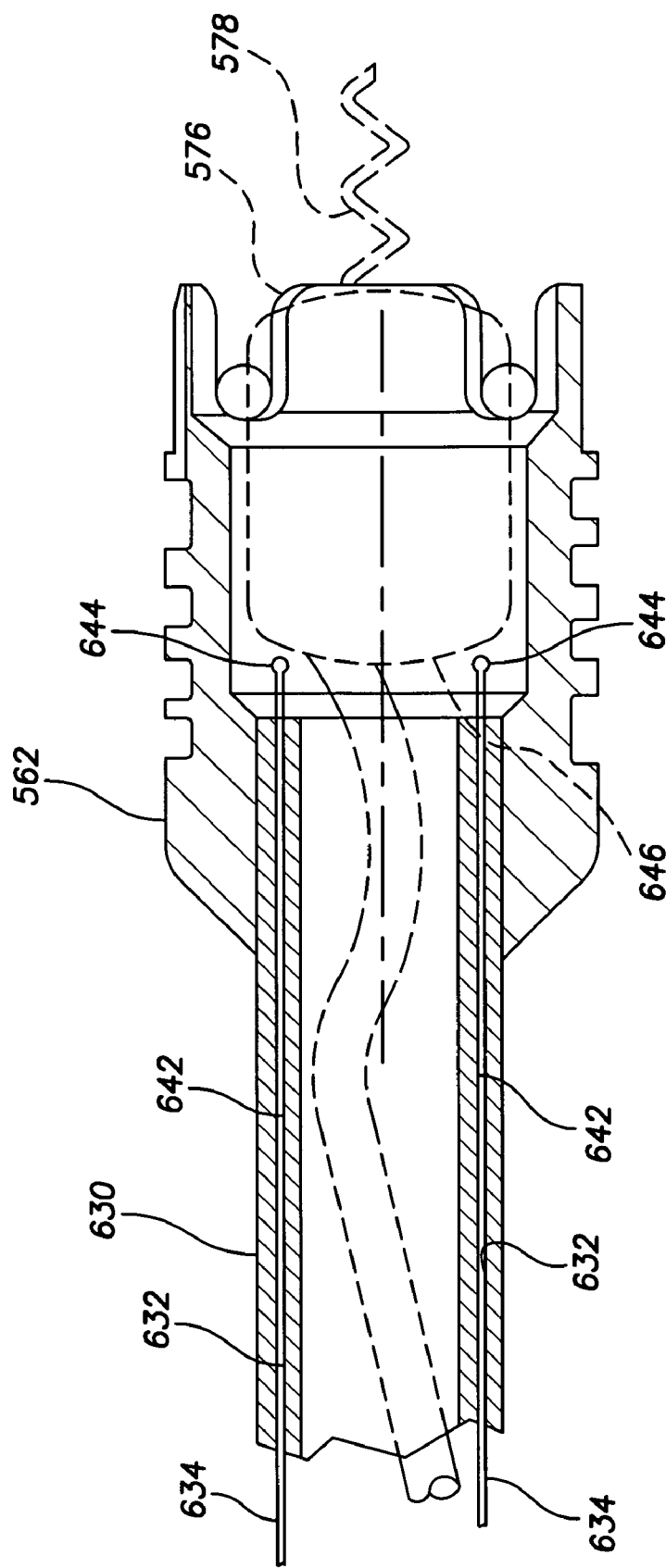
FIG. 27 is a side elevation view, in cross section, of the distal end portion of the steerable introducer of FIG. 26.

Once the electrode header 576 has been implanted by rotating the fixating helix 578 into the target body tissue, the electrode header 576 may be separated from the driver 562 simply by retracting the introducer sheath 502. In most cases such separation will be readily effected. FIGS. 26 and 27 show yet another embodiment of the present invention comprising a mechanism for positively separating the electrode header 576 from the electrode header driver 562 without risk of forcibly withdrawing the implanted helix from the body tissue which might result in trauma. In the embodiment of FIGS. 26 and 27, an inner sheath 630 carries within lumens 632 formed in the wall thereof a pair of parallel, diametrically opposed ejector wires 634 anchored at their proximal ends in a longitudinally displaceable push tube 636 having an end 638 projecting proximally from a handle 640 on the inner sheath 630. The distal extremities 642 of the wires 634 extend from the distal end of the inner sheath 630 into the interior of the header driver 562. An enlargement 644 formed on the distal extremity of each ejector wire 634 is adapted to engage a rear surface 646 of the electrode header when the ejector wires 634 are advanced. A compression spring 648 normally maintains the push tube 636 in a retracted position. It will be seen that manually depressing the push tube 636 will cause the wires 634 to advance until their enlarged ends 642 contact the rear face 646 of the electrode header; further depression of the push tube will cause separation of the electrode header from its driver. By way of example and not limitation, the diameter of each wire 634 may be 0.010 inch and each enlargement 644 may comprise a bead having a diameter of about 0.014 inch. Although two ejector wires are preferred, it will be evident that a single wire may suffice; conversely, more than two wires may be employed.

FIGS. 28-30 show introducers 150, 154 and 156 in accordance with further alternative embodiments of the invention that feature various actuation means for deflecting the flexible distal section of the introducer body. Thus, the introducer 150 of FIG. 28 includes a hand grip 158 carrying a longitudinally slidable ring 160 appropriately connected to the proximal end of a pull cable whose distal end is eccentrically anchored within the flexible distal end section of the introducer body. The introducer 154 of FIG. 29 includes a rotatable knurled thumbwheel 164 whose axis of rotation coincides with the longitudinal axis of the introducer, along the lines of that already described in connection with FIGS. 5-9. Last, the introducer 156 of FIG. 30 features a pivotable hand grip lever 166 the manipulation of which deflects the flexible distal end section of the introducer body.

Figure 31:
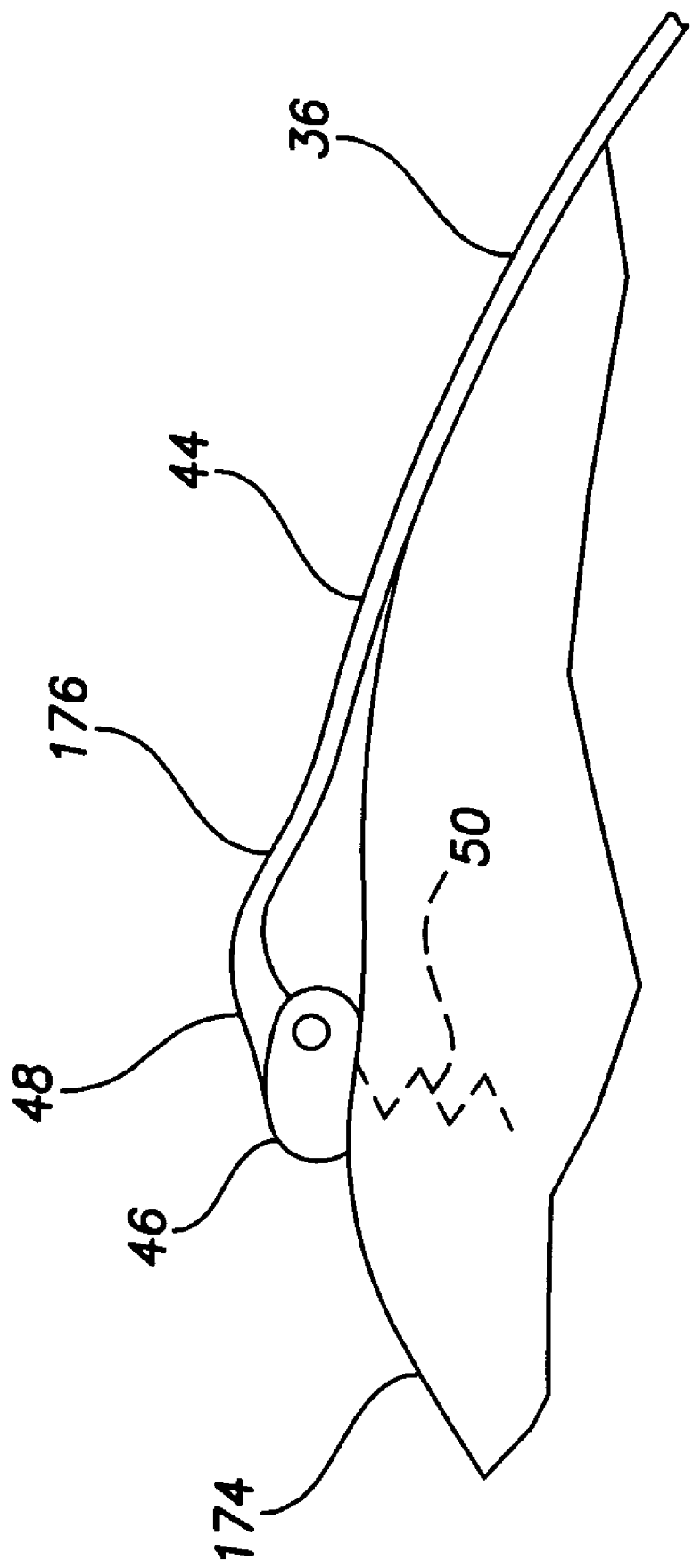
FIG. 31 is a diagrammatic side view of the myocardial lead of FIG. 2 showing its relationship with the outer surface of the heart following implantation.

FIG. 31 shows the electrode header 46 following implantation along the outer surface 174 of a heart. It will be seen that the angle at which the lead body 36 meets the header 46 at the junction 48, which angle, as explained, falls between a purely axially direction and a purely radial direction, permits the lead body 36 to be bent through a gentle curve 176 to lie against the outer surface 174 of the heart and conform to the configuration thereof. To further enhance the ability of the lead body to conform to the curvature of the surface of the heart, the lead body may be made with an oval cross sectional configuration, with the flatter side of the oval section lying against the surface of the heart. Alternatively, for greater flexibility, this section of the lead body may be made of a different, more flexible material, or have a smaller diameter.

Figure 32:
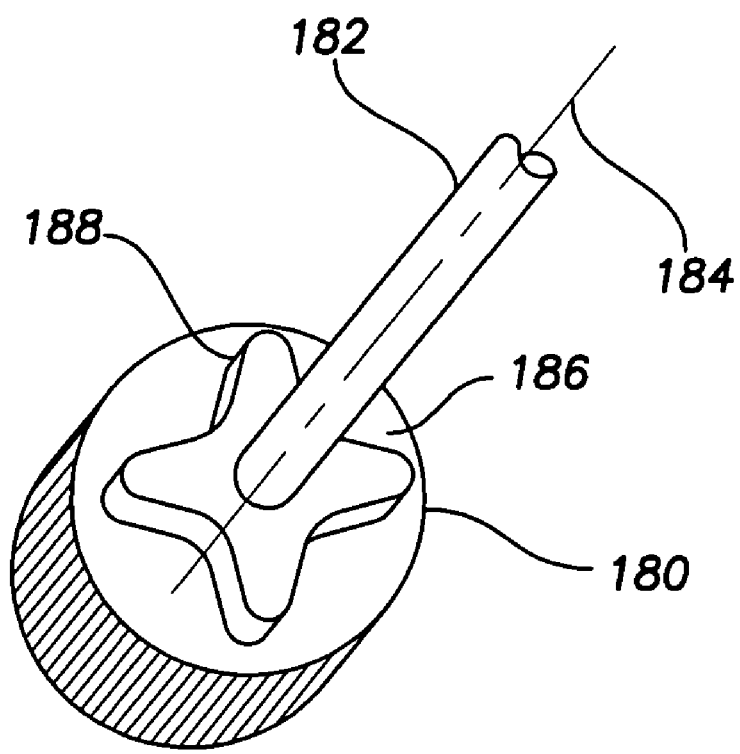
FIG. 32 is a rear, perspective view of an electrode header in accordance with an alternative embodiment of the invention.
Figure 33:
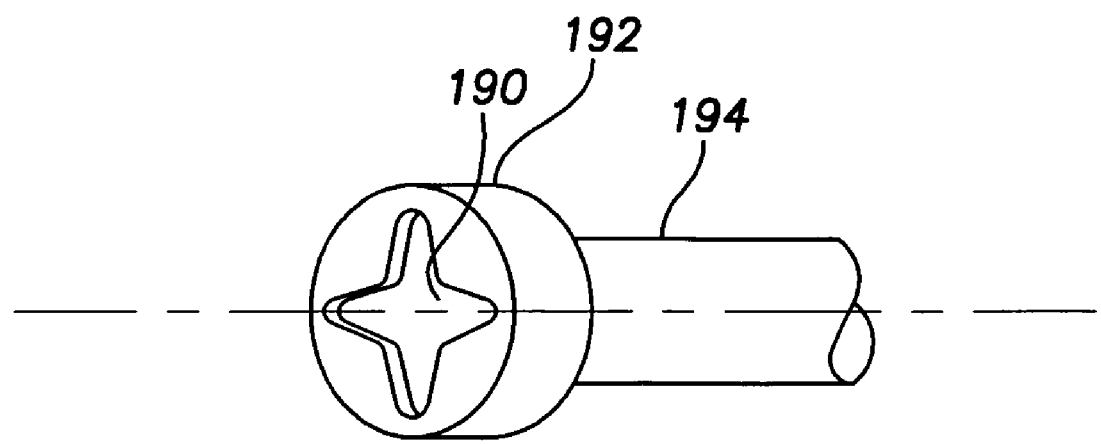
FIG. 33 is a perspective view of the distal end of a driving sheath configured to drivingly engage the electrode header of FIG. 32.
Figure 34:
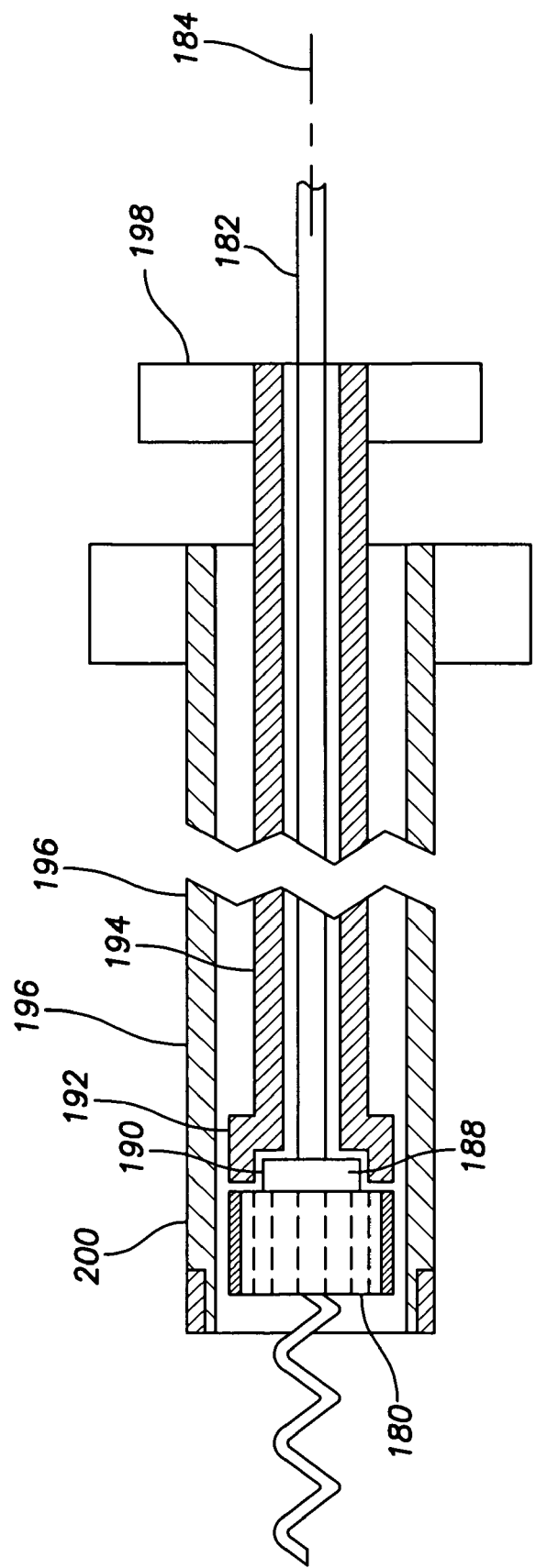
FIG. 34 is a side view, partly in cross section, of an introducer employing the driving sheath of FIG. 33.

FIG. 32 shows an electrode header 180 in accordance with an alternative embodiment of the invention. The electrode header 180 is similar in all respects to that shown in FIGS. 2-4 except that, as shown in FIG. 32, the lead body 182 extends from the proximal end of the electrode header along the central, longitudinal axis 184 of the header. A proximal surface 186 of the header includes a driver projection 188 that may have various configurations but which matches that of a recess 190 in an enlarged distal end 192 of a lead driving sheath 194, seen in FIG. 33. As shown in FIG. 34, the driving sheath 194 is received within an outer tubular introducer body or sheath 196 so as to be movable rotationally and axially relative thereto. The inner driving sheath 194 has a proximal end carrying a handle 198 for moving the inner driving sheath relative to the outer sheath 196. As before, the outer sheath has a flexible or bendable distal end section 200 that may be deflected using any of the various expedients described earlier. Alternatively, the distal end section 200 of the outer sheath may be pre-bent.

Figure 35:
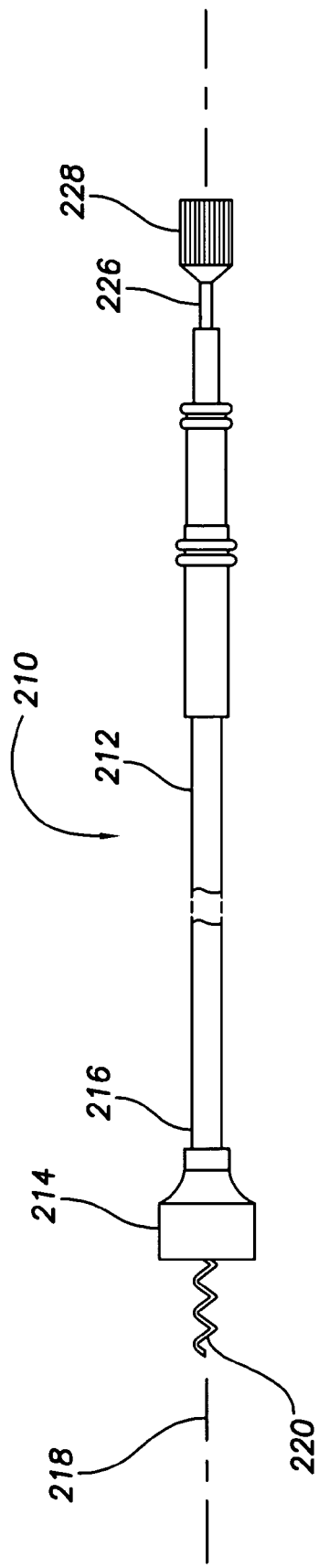
FIG. 35 is a side view of a myocardial pacing and sensing lead in accordance with an alternative embodiment of the present invention.
Figure 36:
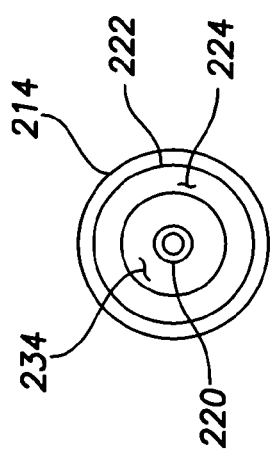
FIG. 36 is a front end view of the electrode header forming part of the lead of FIG. 35.

Turning to FIGS. 35 and 36, there is shown a myocardial lead 210 in accordance with an alternative embodiment of the invention. The myocardial lead 210 is similar in all respects to that shown in FIG. 2 except that the lead 210 comprises a lead body 212 that joins the proximal end of an electrode header 214 at a junction 216 along a central longitudinal axis 218. As before, the electrode header 214 carries a central, cathodic helix electrode 220 and a surrounding, coaxial ring electrode 222 functioning as an anode and having an active, tissue-engaging surface 224 lying in a plane perpendicular to the central axis 218. The lead of FIGS. 35 and 36 is of the type that is implanted by way of an implanting stylet 226, shown in FIGS. 37-39 having a handle 228 at a proximal end and a driver 230 at a distal end that may simply take the form of a slotted screwdriver tip. The driving end 230 of the implanting stylet is received by a corresponding recess or receptacle 232 at the proximal end of the helix electrode, in this case a slot or groove as shown in FIG. 39. It will be evident that mating shapes other than a blade and slot may be used for driving the helix electrode 220. Further, it will be apparent that the helix electrode 220 may be rotationally received within the electrode header 214 so that only the electrode is driven when implanted or, alternatively, the helix electrode 220 may be fixedly secured to the electrode header 214 in which case the entire lead body 212 is rotated upon implantation. As before, a steroid eluting device 234 may be incorporated in the distal end of the electrode header 214.

Figure 37:
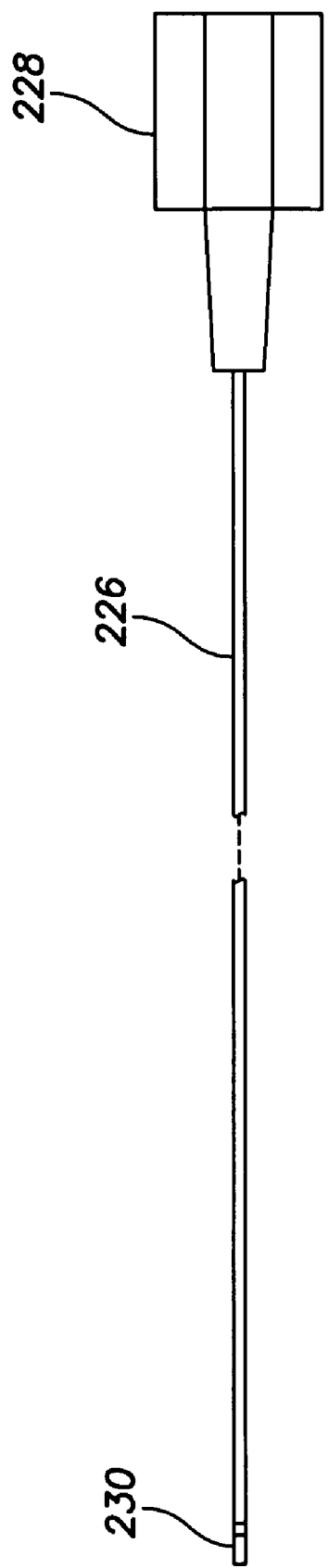
FIG. 37 is a side view of a stylet for implanting the myocardial lead of FIG. 35.
Figure 38:
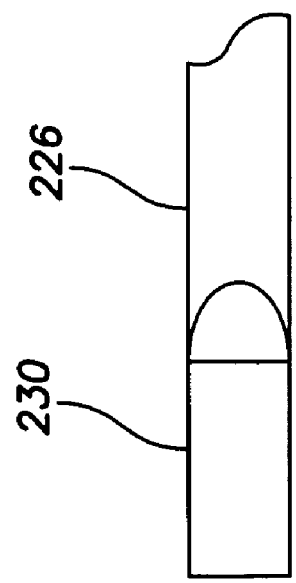
FIG. 38 is an enlarged top plan view of the driving end of the implanting stylet shown in FIG. 37.
Figure 39:
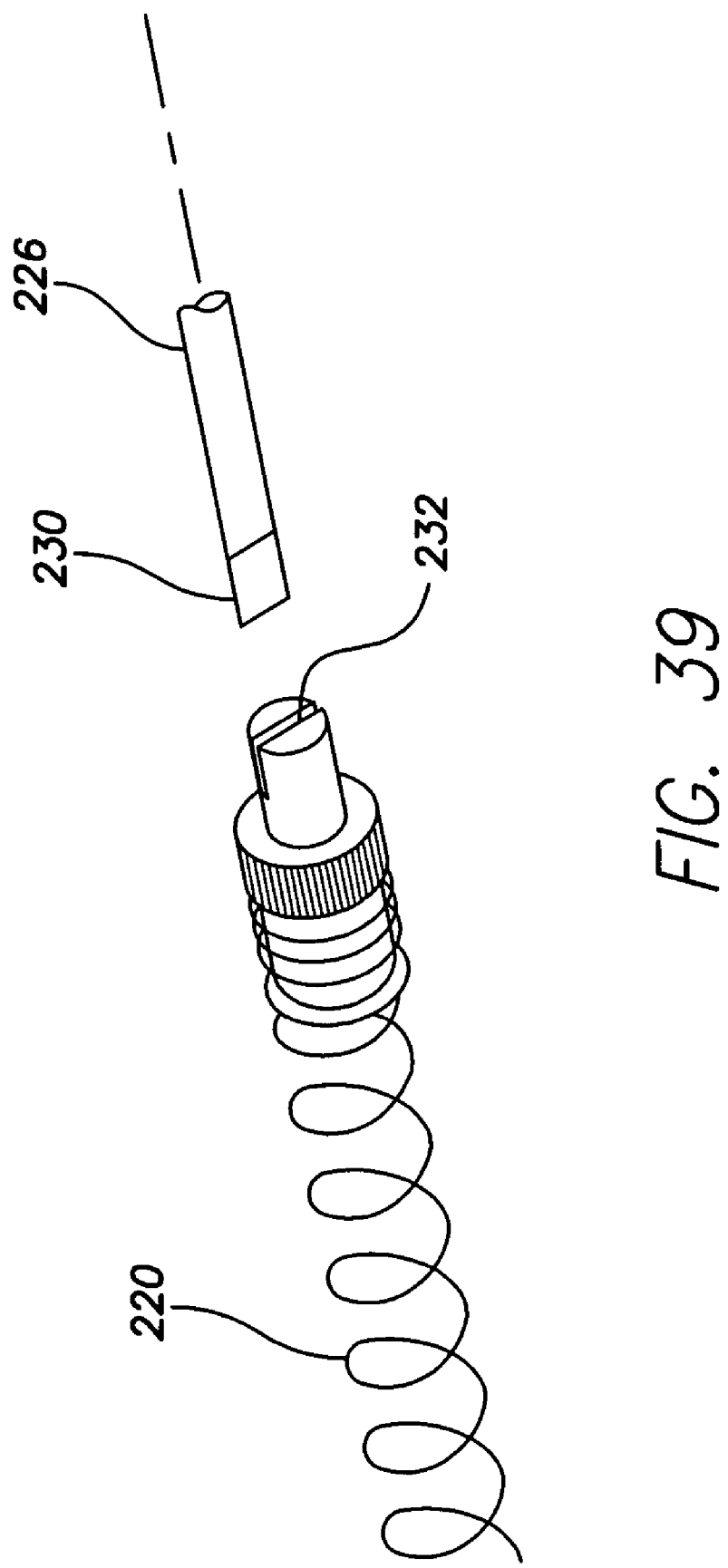
FIG. 39 is a perspective view of a helix electrode assembly that may form part of the myocardial lead of FIG. 35 showing its cooperation with the driving end of the implanting stylet illustrated in FIGS. 37 and 38.

Using the associated implanting stylet 226 shown in FIGS. 37-39, the lead of FIGS. 35 and 36 may be implanted using the alternative introducer embodiments shown in FIGS. 40-43.

Turning first to FIGS. 40 and 41, there is shown an introducer 240 comprising a single, longitudinally extending tubular sheath 242 having a central lumen 244 for receiving the lead body 212. The distal end of the central lumen 244 is enlarged to receive the electrode header 214. The introducer sheath 242 includes adjacent its distal end a corrugated section 246 facilitating the bending or deflection of the distal end of the introducer sheath. Formed in the wall 248 of the sheath and offset from the central axis thereof is a smaller lumen 250 having a blind distal extremity 252 adjacent the distal end of the sheath 242. The smaller lumen 250 is adapted to receive a steering stylet 254 comprising a wire having a proximal end carrying a handle 256 for manipulating the steering stylet to effect bending of the flexible distal end 246 of the introducer sheath. For this purpose, the steering stylet may have a pre-curved distal end portion. As before, the distal tip of the introducer sheath may include a mapping electrode for selecting an optimal helix electrode implantation site. Following implantation of the helix electrode 220 by means of the implanting stylet 226, the introducer is withdrawn from the lead body. It will be evident that for this purpose the central lead body-receiving lumen 244 of the introducer sheath has a diameter that is larger than the connector assembly on the proximal end of the lead body.

Figure 42:
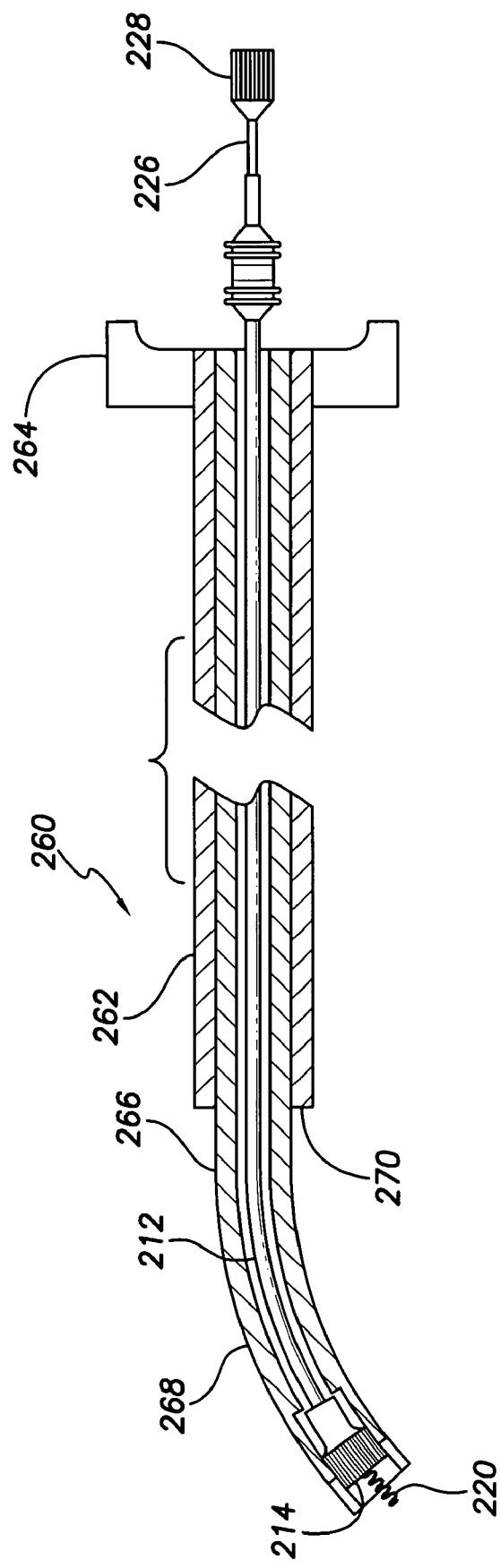
FIG. 42 is a side view, partly in cross section, of another alternative embodiment of the introducer of the invention for inserting and implanting a myocardial lead of the kind illustrated in FIG. 35.

FIG. 42 shows an introducer 260 pursuant to yet another alternative embodiment of the invention for use in implanting a lead of the kind shown in FIGS. 35 and 36. The introducer 260 comprises a straight, rigid outer sheath 262 having a proximal end carrying a handle 264 and an inner sheath 266 having a distal end section 268 projecting from a distal extremity 270 of the outer sheath. The distal end section 268 is pre-bent but can straighten out when retracted into the outer sheath 262. As already explained, implantation of the lead is effected by an implantation stylet 226 the proximal end and handle 228 of which are shown in FIG. 42.

Figure 43:
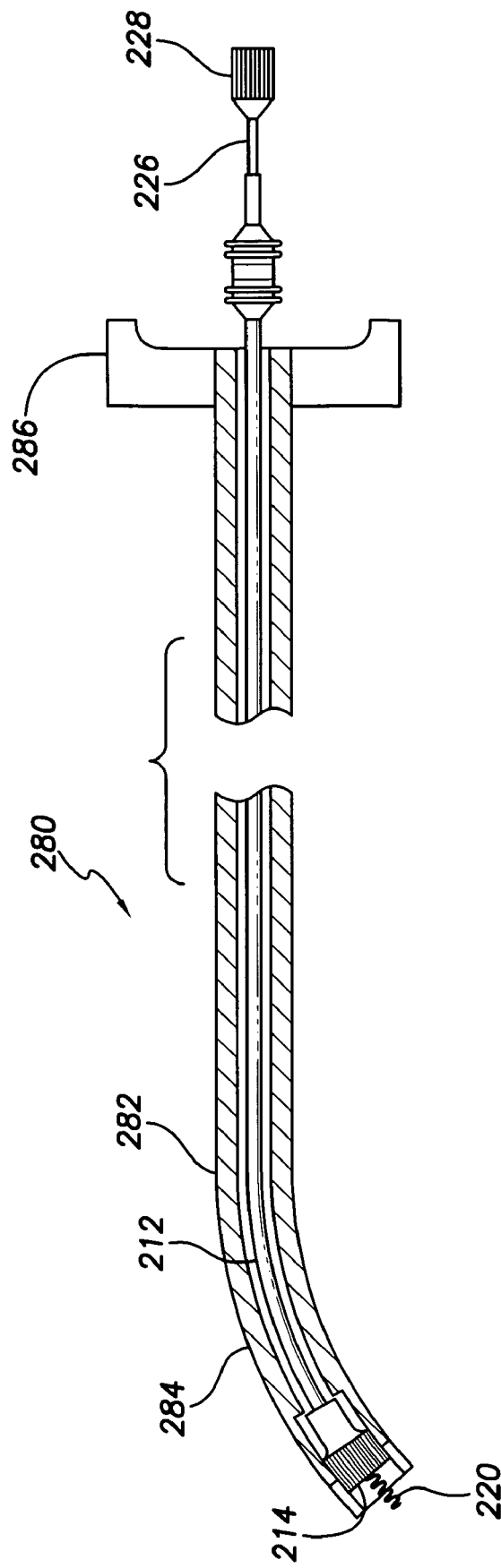
FIG. 43 is a side view, partly in cross section, of yet another alternative embodiment of the introducer of the invention for inserting and implanting a myocardial lead of the kind illustrated in FIG. 35.
Figure 44:
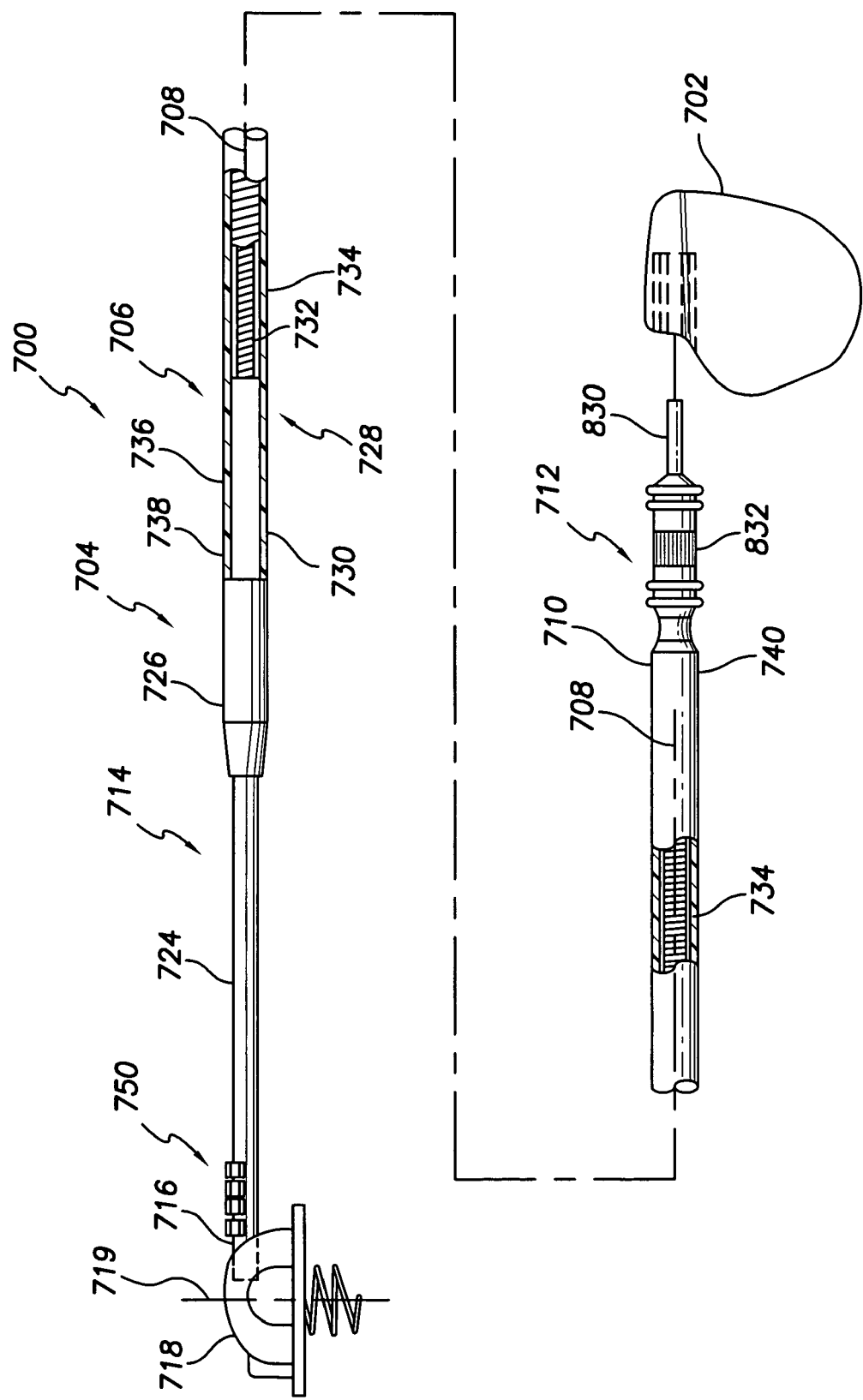
FIG. 44 is a side elevation view of a myocardial pacing and sensing lead system in accordance with an alternative embodiment of the invention.

FIG. 43 illustrates an introducer 280 in accordance with yet another alternative embodiment of the invention for implanting the lead body 212 of FIGS. 35 and 36 using an implanting stylet like that shown in FIGS. 37-39. The introducer 280 comprises a single sheath 282 that is relatively rigid and is provided with a pre-bent distal end section 284 and a handle 286 attached to a proximal end of the sheath.

Referring to FIGS. 44-48, there is shown another specific, exemplary embodiment of the invention comprising an implantable lead system 700 including, generally, a cardiac pacemaker 702 and a myocardial, bipolar active fixation cardiac pacing and sensing lead 704 for connecting the pacemaker with selected myocardium tissue whose electrical activity is to be stimulated and/or sensed. The lead 704 includes a lead body 706 extending along a central, longitudinal axis 708. The lead body 706 has a proximal end 710 carrying a connector assembly 712 for electrically connecting electrical conductors within the lead body 706 to the pacemaker 702. The lead body 706 further comprises a distal end 714 having a distal extremity 716 carrying a bipolar, active fixation, steroid-eluting electrode header 718 having a vertical central axis 719.

The distal end 714 of the lead body comprises a bilumen, tubular structure molded as a single, unitary part from silicone rubber or the like, for example, Dow Corning specification Silastic 7-6860 biomedical grade liquid silicone rubber (LSR). The molded distal end 714 of the lead body defines a pair of longitudinally extending, spaced apart lumens 720 and 722 for receiving electrical conductors to be described.

The distal end 714 comprises a small diameter, flexible, distal section 724; a larger diameter transition section 726; and a proximal stepped section 728. The stepped section 728 comprises a first length 730 of somewhat smaller diameter than the transition section 726 from which the first length extends and a second length 732 projecting proximally from the first length 730 and having a smaller diameter than the first length. Wound around the second length 732 is the distal end of a strain relief coil 734 that extends proximally from the second length 732. Preferably, the strain relief coil 734 extends from the second length 732 to the proximal end 710 of the lead body 706. The coil 734 may be fabricated of metal wire having a diameter of, for example, 0.004 inch. The strain relief coil 734 is not connected to conduct electrical current; its sole purposes are to protect the lead body against undue or extreme bending and to prevent kinking or crushing of the lead body by the patient's ribs or other crush force-bearing means.

The lead body 706 further comprises an insulating tubular housing 736 of silicone rubber or the like having a distal extremity 738 abutting the proximal end of the transition section 726 and a proximal extremity 740 adjacent to the connector assembly 712. The tubular housing 736 has an outer diameter substantially the same as that of the transition section 726 so as to define a smooth, isodiametric outer surface. The tubular insulating housing 736 overlies the strain relief coil 734.

The greater degree of flexibility of the distal section 724 of the distal end may be achieved by providing the distal section with a smaller outer diameter (as shown) or fabricating that section of a different, more "floppy" material. Further, the section 724 may be tapered or stepped to a smaller diameter toward the electrode header. By way of example and not limitation, the flexible distal section 724 may have a uniform diameter of 0.065 inch and a length of 1 3/16 inches.

Figure 45:
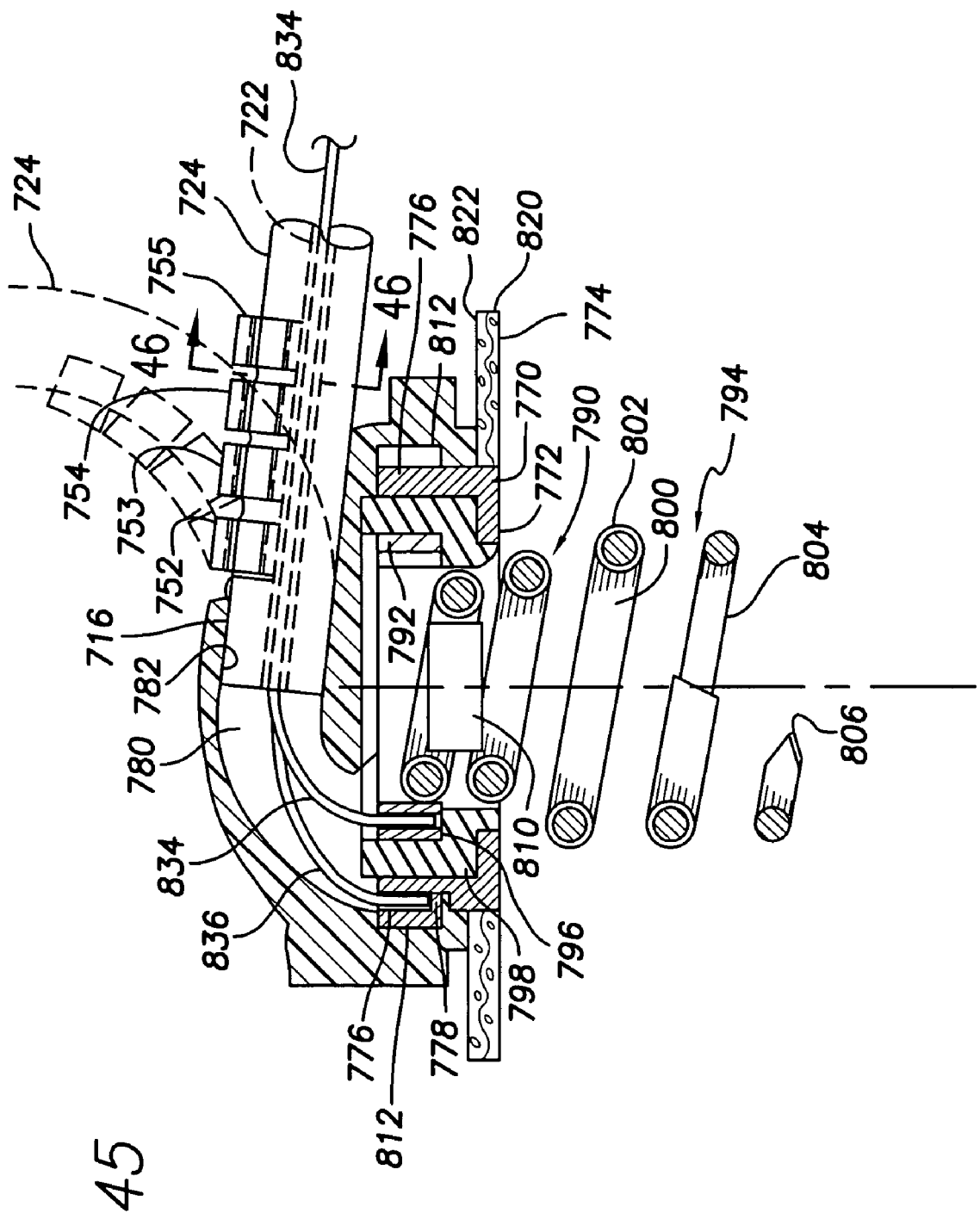
FIG. 45 is an enlarged side elevation view, in cross section, of an electrode header forming part of the system of FIG. 44.
Figure 46:
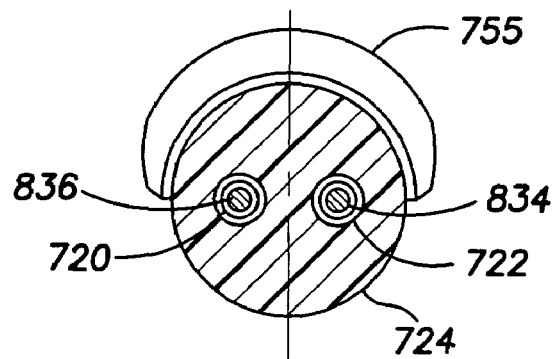
FIG. 46 is a cross section view of the distal end portion of a lead body forming part of the system of FIG. 44, as seen along line 46-46 in FIG. 45.
Figure 47:
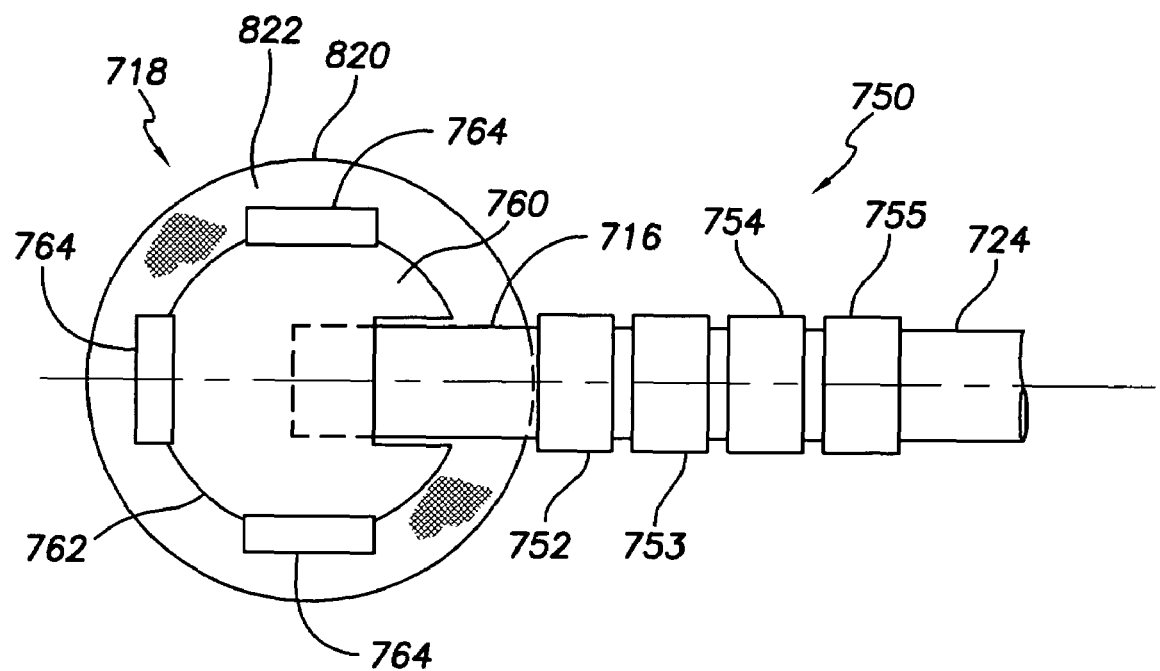
FIG. 47 is a top plan view of the electrode header shown in FIG. 45.
Figure 48:
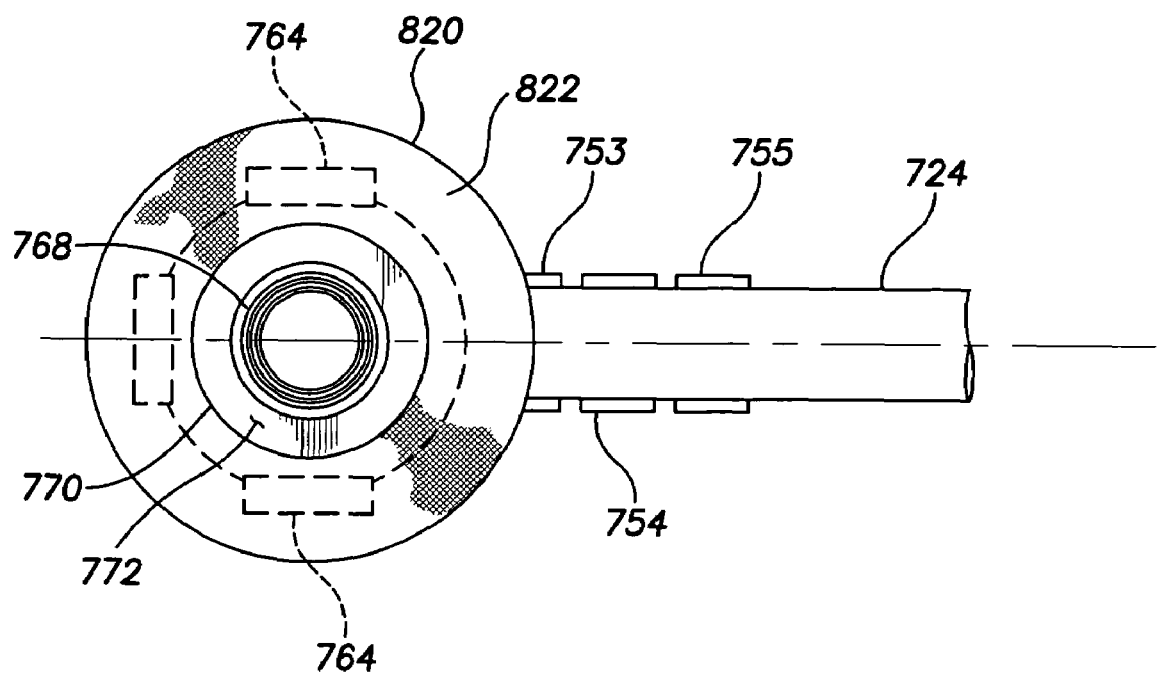
FIG. 48 is a bottom plan view of the electrode header shown in FIG. 45.
Figure 49:
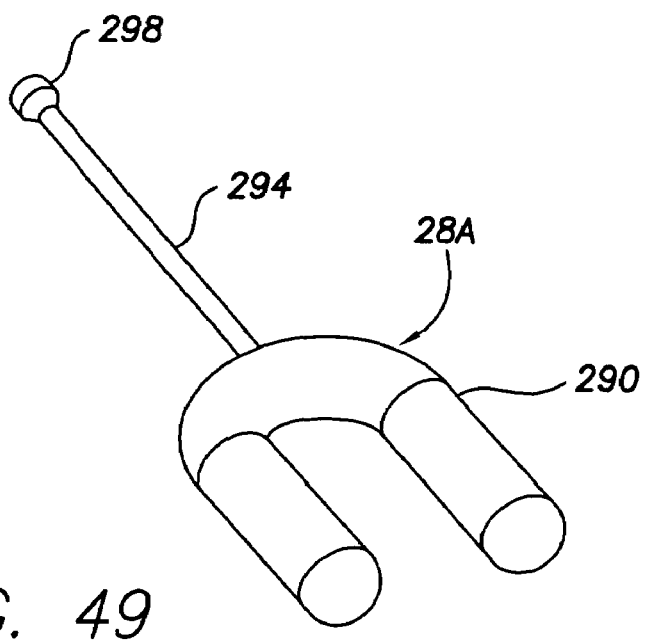
FIGS. 49-52 are perspective views of alternative embodiments of inflatable heart jacks for use with the myocardial implantation system of the present invention.
Figure 52:
Figure 51:
Figure 50:

In the embodiment shown, the flexible distal section 724 may exit the electrode header in a direction perpendicular to the central axis 719 to provide good conformity between the flexible section and the curved heart surface to which the electrode header 718 is attached. Preferably, as shown in FIG. 45, the flexible section 724 may exit the electrode header 718 at a slightly acute angle relative to the vertical axis 719 thereby gaining even better conformity to the curved heart surface. Alternatively, the flexible section 724 may extend away at an obtuse angle relative to the axis 719 to facilitate loading in the delivery introducer. As explained earlier, the distal end 714 of the lead body is typically adapted to assume a curved configuration within the lumen of an introducer so that, with the distal end 714 contained or tunneled within the lumen of the introducer, the wrapping problem of existing systems is avoided. Generally, the flexible distal section 714 may exit the header 718 at any angle ranging from in-line with the vertical central axis 719 to perpendicular to that axis, or at a slightly acute angle thereto, as seen in FIG. 45.

The flexible distal section 724 of the lead body's distal end 714 includes a strain relief feature 750 providing resistance against extreme bending of the section 724. More specifically, in accordance with the specific, exemplary embodiment shown in FIGS. 44-48, molded with the flexible distal section 724 of the lead body is a plurality of longitudinally spaced apart projections 752-755 extending outwardly from the outer surface of the flexible section 724 adjacent to the distal extremity 716 at the junction of the lead body 706 and the header 718. It will be seen that upward bending of the flexible section 724 (as depicted by the broken lines in FIG. 45) will cause adjacent ones of the projections 752-755 to interfere with one another so as to resist and restrict further bending. The height of the projections, their spacing, and so forth will determine the radius of curvature at which the projections will tend to resist further bending. Preferably, as shown in FIGS. 44-48, the projections 752-755 comprise a linear array of ribs extending from only an upper portion of the circumference of the flexible distal section 724 since it is only bending in the upward direction (as seen in FIG. 45) that needs to be resisted. Although four projections are shown, it will be evident that any number, two or more, may be used. Furthermore, it will be evident to skilled artisans that the spacing and height of the projections may be selected so that there will be no appreciable resistance to the moderate bending of the lead when it is loaded in the introducer, while providing resistance to bending beyond that.

The header 718 comprises a body 760 molded of silicone rubber or the like. The header body 760 preferably has a generally low profile, dome shape with a side surface 762 carrying at least one and preferably a plurality of radially projecting lugs 764 shaped and positioned for engagement by an introducer of the kind and in the fashion described earlier herein for both holding and rotating the header. The header 718 carries a helical, screw-in fixation element or helix 768 coaxial of the central axis 719 and adapted to be screwed into cardiac tissue in the manner that has been described previously. The header 718 further has a TiN-coated ring electrode 770 concentric with the helix 768 and having a lower, tissue-engaging planar surface 772 flush with a lower, planar surface 774 of the header. The ring electrode 770 has an upstanding portion 776 having a socket 778 for receiving an electrical conductor. The header body 760 defines a cavity 780 communicating with a proximally-facing receptacle 782 that receives the distal extremity 716 of the distal end 714 of the lead body. The screw-in helix 768 may be electrically inactive or, as is the case in the embodiment of FIGS. 44-48, may be electrically active and function as the cathode of a bipolar pacing and sensing lead system, with the ring electrode 770 typically functioning as an anode.

The helix 768, which in the embodiment shown is electrically active, has a stepped configuration comprising a first, smaller diameter series of turns 790 nested within and welded to an electrically conductive annular helix coupler 792 and a second, larger diameter series of exposed turns 794 projecting from the lower planar surface 774 of the electrode header. The helix coupler 792 has a socket 796 for receiving an electrical conductor. An electrically insulating ring 798 is sandwiched between the helix coupler 792 and the ring electrode 770 so as to maintain electrical isolation between these elements.

In one specific, exemplary form, the wire used for forming the helix 768 may comprise TiN-coated, 80/20 platinum/iridium alloy having a diameter of 0.020 inch. The larger diameter, exposed portion of the helix may comprise 1 turn to 4 turns having a constant outer diameter of 3.91 mm (0.154 inch) while the smaller diameter portion of the helix within the header may comprise approximately 2 turns having a uniform outer diameter of 2.89 to 2.99 mm (0.114-0.118 inch). In its preferred form, the helix 768 has a conventional right hand sense so that clockwise rotation (as viewed, as in FIG. 47, looking down on the top of the header) screws the helix into the tissue. It will be understood that the foregoing parameters are exemplary only and are not to be taken in a limiting sense.

The helix 768 has an electrically masked or insulated section 800 coated with an insulator 802 such as parylene, silicone, polyurethane or paralast and an electrically uninsulated tip section 804 having a sharp conical or multifaceted point 806. The unmasked tip section 804 may have a surface area of, for example, 4 to 10 mm2 for 2 to 3 exposed turns, with a preferred surface area of 4 to 5 mm2. The small surface area of the bare tip section 804 decreases pacing thresholds and increases pacing impedance. Whether electrically active or inactive, the helix 768, when advanced into the selected cardiac tissue, serves to stabilize or anchor the header 718 relative to the cardiac tissue, with an annular mesh element, described below, adding further stability to the anchoring of the electrode header. The smaller turns 790 of the helix carry, within the confines of the electrode header, a drug-permeated, monolithic controlled release device (MCRD) 810 for dispensing a steroid or other drug at the stimulation site.

The helix 768, helix coupler 792, ring electrode 770 and insulating ring 798 may comprise a prefabricated assembly pressed into the lower portion of the cavity 780 of the molded header body 760 and retained therein by ears 812 projecting from the upstanding portion 776 of the ring electrode 770 into corresponding recesses formed in the header body.

Adhesively bonded to the lower planar surface 774 of the electrode header 718 is an annular anchoring element in the form of a biocompatible, biostable mesh 820 extending about the ring electrode 770 and having an outwardly projecting rim 822. The mesh 820 may comprise, by way of example, a polyester mesh fabric knitted or woven from thin, texturized multifilament yarn. The more porous mesh thus produced promotes substantial tissue ingrowth to aid in securely anchoring the electrode header to the myocardial tissue. The mesh may have a thickness of 0.36 mm, by way of example. A texturized mesh fabric meeting the required specifications is manufactured by Vascutek Ltd.; such mesh has been used for carotid artery grafts. An appropriate medical adhesive may serve to bond the mesh to the lower planar surface of the electrode header. Alternatively, the portion of the mesh radially inward of the projecting rim 822 may be molded into the lower surface of the header body. Instead of texturized polyester mesh fabric, other materials, such as velour, may be used.

The connector assembly 712 carried by the proximal end portion of the lead body is adapted to electrically and mechanically couple the lead body 706 to the pacemaker 702. For the bipolar embodiment under consideration, the connector assembly may conform to the IS-1 standard including coaxial terminal contacts in the form of a pin terminal contact 830 and a ring terminal contact 832 positioned to engage corresponding electrical terminals within a receptacle of the pacemaker 702. The pin terminal contact 830 is electrically connected to the socket 796 on the helix coupler 792 by a first electrical conductor 834 passing through the tubular lead body housing 736, through one of the lumens 720, 722 in the molded distal end 714 and into the cavity 780 within the electrode header. Similarly, the ring terminal contact 832 is electrically connected to the socket 778 on the ring anode electrode 770 by a second electrical conductor 836 passing through the tubular lead body housing 736, through the other of the lumens 720, 722 in the molded distal end 714 and into the cavity 780 within the electrode header. Although the electrical conductors 834 and 836 may take various forms, including coil conductors, they preferably comprise 1×19 strand ETFE coated cable conductors fabricated of MP35N-LT (low titanium) alloy.

With reference to FIGS. 49-52, there are shown four embodiments 28A, 28B, 28C and 28D of the heart jack 28 (FIG. 1) for lifting the heart for access to the posterior portions thereof. The heart jacks 28A-28D comprise inflatable balloons 290-293, respectively, at the distal ends of air introduction lines 294-297 whose proximal ends carry fittings 298-301 for attachment to a valve-controlled pressurized air supply (not shown). A heart jack is inserted through a trocar inserted in one of the incisions such as the incision 16 in its deflated, furled configuration (FIG. 1). The heart jack is then maneuvered into the desired position under observation through the visualization instrument 24 and upon reaching the desired location is inflated so as to fully deploy the jack. The heart jack's inflatable balloons may take any of a number of configurations suitable for elevating various remote portions of the surface of the heart.

While several illustrative embodiments of the invention have been shown and described, numerous variations and alternative embodiments will occur to those skilled in the art. Such variations and alternative embodiments are contemplated, and can be made without departing from the spirit and scope of the invention as defined in the appended claims.

What is claimed is:

1. An implantable epicardial stimulation lead comprising:
   a lead body having a distal end and a proximal end;
   an electrical connector carried by the proximal end of the lead body; and
   an electrode header carried by the distal end of the lead body, the electrode header having a header body with a substantially planar distal tip surface, the electrode header having an axis and including a helical fixation element extending along said axis and extending distally from the planar distal tip surface, the electrode header having a ring electrode disposed at the planar distal tip surface, the electrode header having an outer surface configured to receive a driver for rotating the electrode header to screw the helical fixation element into heart tissue, the lead body carrying along its length a strain relief member resisting excessive bending of the lead body;
   wherein a plurality of pins project radially outwardly from the outer surface of the electrode header, the plurality of pins engaging with the driver to rotate the electrode header to screw the helical fixation element into the heart tissue; and
   wherein said strain relief member comprises a longitudinally disposed strain relief coil extending proximally of the distal end of the lead body, and wherein the strain relief coil is disposed within the lead body and permanently fixated to the lead body.

2. The lead of claim 1, wherein:
   the strain relief coil extends between the distal and proximal ends of the lead body.

3. The lead of claim 1, wherein:
   the strain relief coil is made of metal but is not connected to conduct electrical current.

4. The lead of claim 1, wherein:

the lead body further comprises an outer, tubular, insulating housing overlying the strain relief coil and extending from the distal end of the lead body to the proximal end of the lead body, and the outer, tubular, insulating housing is not part of an introducer.

5. The lead of claim 4, wherein:

at the junction of the outer, tubular, insulating housing and the electrode header, the outer, tubular, insulating housing extends away from the electrode header in a direction that falls between the axis of the electrode header and a radial direction perpendicular to the axis of the electrode header such that the outer, tubular, insulating housing conforms to an outer surface of the heart after implantation.

6. The lead of claim 1, wherein:

the driver has longitudinally extending slots to receive the plurality of pins, and the driver is a portion of an introducer.

7. The lead of claim 1, wherein:

at a junction of the lead body and the electrode header, the lead body extends away from the electrode header in a direction that falls between the axis of the electrode header and a radial direction perpendicular to the axis of the electrode header such that the lead body conforms to an outer surface of the heart after implantation.

8. The lead of claim 1, wherein:

an outer diameter of the electrode header is at least three times greater than an outer diameter of the lead body.

9. An implantable epicardial stimulation lead system comprising:

an introducer comprising:

an introducer body having an inner sheath extending from a proximal portion to a distal portion of the introducer body;

a handle at the proximal end of the introducer body;

an electrode header driver at the distal portion of the introducer body, the electrode header driver having a matable surface; and an implantable epicardial stimulation lead comprising:

a lead body having a distal end and a proximal end, the lead body configured to be received within the inner sheath of the introducer body;

an electrical connector carried by the proximal end of the lead body;

an electrode header carried by the distal end of the lead body and having an outer surface and a planar distal tip surface, the electrode header having an axis and including a helical fixation element extending along the axis and extending distally from the planar distal surface, the electrode header having a ring electrode disposed at the planar distal tip surface, the electrode header driver configured to receive the electrode header; and a plurality of pins projecting radially outwardly from the outer surface of the electrode header, the plurality of pins engaging with the matable surface of the electrode header driver to rotate the electrode header to screw the helical fixation element into heart tissue;

wherein an outer diameter of the electrode header is at least three times greater than an outer diameter of the lead body;

a strain relief member carried along the length of the lead body, the strain relief member disposed within the lead body and permanently fixated to the lead body the strain relief member configured to resist excessive bending of the lead body.

10. The lead system of claim 9, wherein:

said strain relief member comprises a longitudinally disposed strain relief coil extending proximally of the distal end of the lead body.

11. The lead of claim 9, wherein:

the strain relief coil extends between the distal and proximal ends of the lead body.

12. The lead of claim 9, wherein:

the strain relief coil is made of metal but is not connected to conduct electrical current.

13. The lead of claim 9, wherein:

the lead body further comprises an outer, tubular, insulating housing overlying the strain relief coil and extending from the distal end of the lead body to the proximal end of the lead body, and the outer, tubular, insulating housing is not part of the introducer.

14. The lead of claim 13, wherein:

at the junction of the outer, tubular, insulating housing and the electrode header, the outer, tubular, insulating housing extends away from the electrode header in a direction that falls between the axis of the electrode header and a radial direction perpendicular to the axis of the electrode header such that the outer, tubular, insulating housing conforms to an outer surface of the heart after implantation.

15. The lead of claim 9, wherein:

the electrode header driver has longitudinally extending slots to receive the plurality of pins.

16. The lead of claim 9, wherein:

at the junction of the lead body and the electrode header, the lead body extends away from the electrode header in a direction that falls between the axis of the electrode header and a radial direction perpendicular to the axis of the electrode header such that the lead body conforms to an outer surface of the heart after implantation.

* * * * *